(12) United States Patent
Smith et al.

(10) Patent No.: US 7,486,855 B2
(45) Date of Patent: Feb. 3, 2009

(54) OPTICAL MICRORESONATOR

(75) Inventors: Terry L. Smith, Roseville, MN (US);
Yasha Yi, Woodbury, MN (US); Barry J. Koch, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/616,338

(22) Filed: Dec. 27, 2006

(65) Prior Publication Data

US 2008/0159683 A1 Jul. 3, 2008

(51) Int. Cl.
*G02B 6/26* (2006.01)

(52) U.S. Cl. ............................. 385/32; 385/30

(58) Field of Classification Search .................. 385/30, 385/32
See application file for complete search history.

(56) References Cited

U.S. PATENT DOCUMENTS

| | | | |
|---|---|---|---|
| 4,185,257 A * | 1/1980 | Nakajima | .................... 333/208 |
| 4,775,214 A | 10/1988 | Johnson | |
| 5,398,256 A * | 3/1995 | Hohimer et al. | ................ 372/94 |
| 5,420,880 A | 5/1995 | Tabatabaie et al. | |
| 5,537,432 A * | 7/1996 | Mehuys et al. | ............ 372/50.11 |
| 5,651,018 A * | 7/1997 | Mehuys et al. | ............. 372/50.1 |
| 5,748,663 A * | 5/1998 | Chenausky | ................... 372/64 |
| 5,910,963 A * | 6/1999 | Simon | .......................... 372/98 |
| 6,009,115 A * | 12/1999 | Ho | .............................. 372/92 |
| 6,286,262 B1 | 9/2001 | Prevot et al. | |
| 6,490,039 B2 | 12/2002 | Maleki et al. | |
| 6,515,749 B2 | 2/2003 | Pipino | |
| 6,580,851 B1 | 6/2003 | Vahala et al. | |
| 6,583,399 B1 | 6/2003 | Hunziker et al. | |
| 6,608,716 B1 | 8/2003 | Armstrong et al. | |
| 6,657,731 B2 | 12/2003 | Tapalian et al. | |
| 6,661,950 B1 | 12/2003 | Strecker | |
| 6,680,962 B2 * | 1/2004 | Liu et al. | ....................... 372/94 |
| 6,711,200 B1 | 3/2004 | Scherer et al. | |
| 6,751,368 B2 | 6/2004 | Lim et al. | |
| 6,772,480 B2 | 8/2004 | Prevot et al. | |
| 6,781,690 B2 | 8/2004 | Armstrong et al. | |
| 6,795,481 B2 * | 9/2004 | Maleki et al. | ............... 372/108 |
| 6,876,796 B2 | 4/2005 | Garito et al. | |
| 6,901,101 B2 | 5/2005 | Frick | |

(Continued)

FOREIGN PATENT DOCUMENTS

WO     WO 98/53535     11/1998

(Continued)

OTHER PUBLICATIONS

U.S. Appl. No. 11/277,769, filed Mar. 29, 2006, entitled "Coupling Light Into Microresonators,".

(Continued)

*Primary Examiner*—K. Cyrus Kianni
(74) *Attorney, Agent, or Firm*—Robert S. Moshrefzadeh

(57) ABSTRACT

An optical microresonator system and a sensor system incorporating same are disclosed. The optical microresonator system includes an optical waveguide and an optical microcavity that is optically coupled to the optical waveguide. The microcavity is capable of supporting primarily one or more resonant modes. The optical microresonator system further includes an optical microresonator that is optically coupled to the microcavity and is capable of supporting a resonant mode.

18 Claims, 19 Drawing Sheets

U.S. PATENT DOCUMENTS

| | | | |
|---|---|---|---|
| 6,947,632 | B2 | 9/2005 | Fischer et al. |
| 7,062,131 | B2 | 6/2006 | Ilchenko |
| 7,085,452 | B1 * | 8/2006 | Lin et al. .................. 385/39 |
| 7,271,379 | B2 | 9/2007 | Fan et al. |
| 7,292,112 | B2 * | 11/2007 | Oxborrow .................. 331/96 |
| 2002/0122179 | A1 | 9/2002 | Pipino |
| 2003/0063426 | A1 | 4/2003 | Smirnov et al. |
| 2003/0202555 | A1 * | 10/2003 | Liu et al. .................. 372/94 |
| 2003/0231826 | A1 | 12/2003 | Boyd et al. |
| 2004/0023396 | A1 | 2/2004 | Boyd et al. |
| 2004/0137478 | A1 | 7/2004 | Arnold et al. |
| 2004/0247008 | A1 | 12/2004 | Scheuer et al. |
| 2005/0003520 | A1 | 1/2005 | Misiakos et al. |
| 2005/0013529 | A1 | 1/2005 | Chiu et al. |
| 2005/0018274 | A1 | 1/2005 | Halas et al. |
| 2005/0077513 | A1 | 4/2005 | Fan et al. |
| 2005/0078731 | A1 | 4/2005 | Fan et al. |
| 2005/0141809 | A1 | 6/2005 | Gardner et al. |
| 2005/0210989 | A1 | 9/2005 | Ja et al. |
| 2005/0226564 | A1 | 10/2005 | Gardner et al. |
| 2005/0263679 | A1 | 12/2005 | Fan et al. |
| 2005/0286602 | A1 * | 12/2005 | Gunn et al. .................. 372/94 |
| 2006/0062508 | A1 | 3/2006 | Guo et al. |
| 2006/0170931 | A1 | 8/2006 | Guo et al. |
| 2007/0001773 | A1 * | 1/2007 | Oxborrow .................. 331/154 |
| 2007/0147445 | A1 * | 6/2007 | Ishaaya et al. ......... 372/29.023 |

FOREIGN PATENT DOCUMENTS

| | | |
|---|---|---|
| WO | WO 01/40757 | 6/2001 |
| WO | WO 2005/116615 | 12/2005 |

OTHER PUBLICATIONS

U.S. Appl. No. 11/565,920, filed on Dec. 1, 2006, entitled "Optical Sensing Device,".

U.S. Appl. No. 11/565,955, filed Dec. 1, 2006 entitled "Optical Sensing Methods,".

U.S. Appl. No. 11/565,935, filed Dec. 1, 2006 entitled "Optical Microresonator,".

U.S. Appl. No. 11/617,923, filed Dec. 29, 2006, entitled "Optical Sensing Devices and Methods,".

U.S. Appl. No. 11/617,932, filed Dec. 29, 2006, entitled "Optical Sensing Devices and Methods,".

Brun et al., "Coupling nanocrystals to a high-Q silica microsphere: Entanglement in quantum dots via photon exchange," *Physical Review A*, vol. 61, pp. 032307-1-5 (2000).

Fan et al., "Coupling semiconductor nanocrystals to a fused-silica microsphere: a quantum-dot microcavity with extremely high Q factors," *Optics Letters*, vol. 25, No. 21 pp. 1600-1602 (Nov. 1, 2000).

Fano, "Effects of Configuration Interaction on Intensities and Phase Shifts," *Physical Review*, vol. 124, No. 6, pp. 1866-1878 (Dec. 15, 1961).

Götzinger et al., "Towards controlled coupling between a high-Q whispering-gallery mode and a single nanoparticle," *Appl. Phys. B*, vol. 73, pp. 825-828 (2001).

Little et al., "Second-order filtering and sensing with partially coupled traveling waves in a single resonator", *Optics Letters*, vol. 23, No. 20, pp. 1570-1572 (Oct. 15, 1998).

Soller et al., "Dynamic modifications to the plasmon resonance of a metallic nanoparticle coupled to a planar waveguide: beyond the point-dipole limit," *J. Opt. Soc. Am. B.*, vol. 19, No. 5, pp. 1195-1203 (May 2002).

Xu, et al., "Scattering-theory analysis of waveguide-resonator coupling," *Physical Review E*, vol. 62, No. 5, pp. 7389-7404 (Nov. 2000).

* cited by examiner

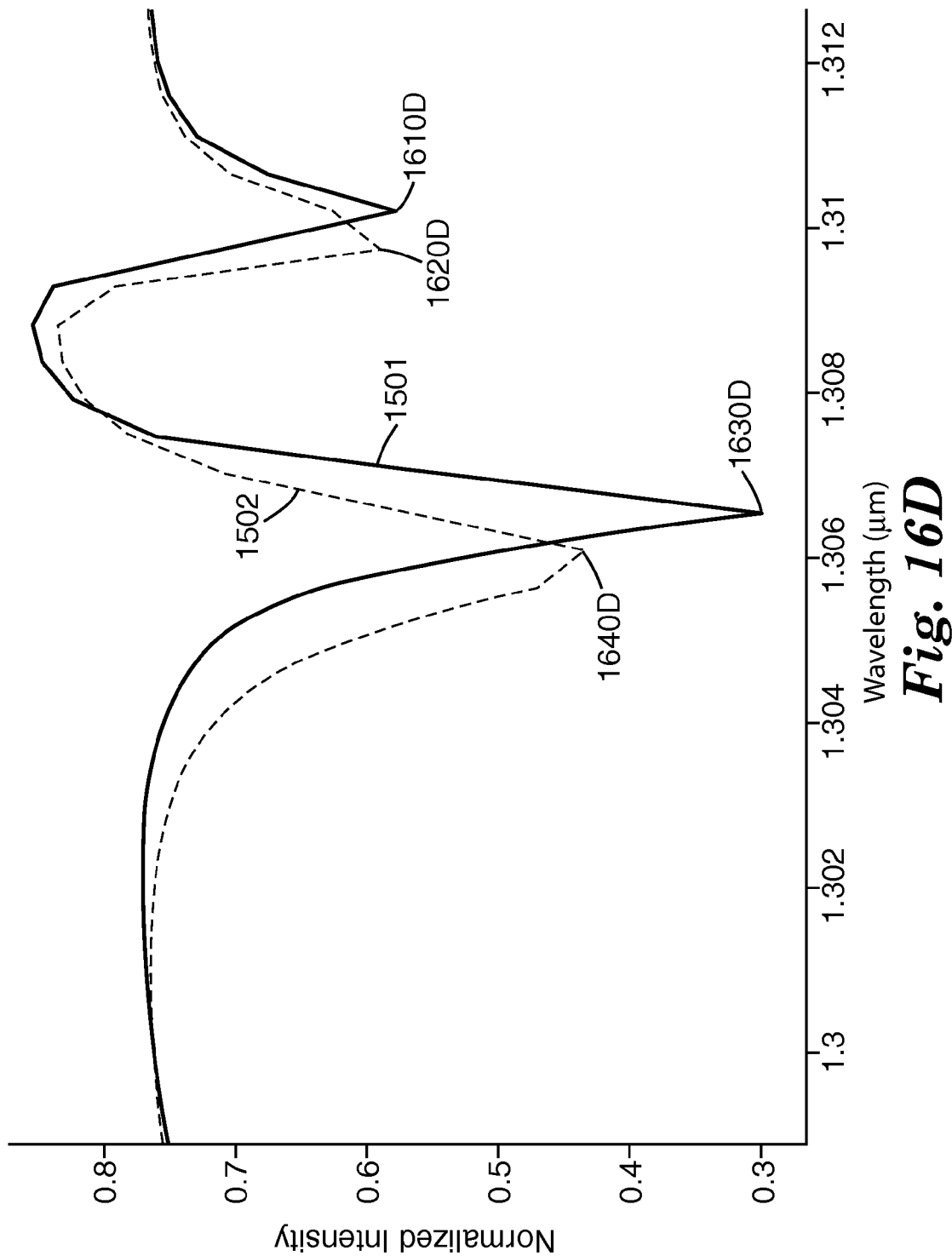

OPTICAL MICRORESONATOR

FIELD OF THE INVENTION

This invention generally relates to optical devices. The invention is particularly applicable to optical devices such as optical sensors, that incorporate microresonators.

BACKGROUND

Microresonators have received increasing attention in various applications such as optical switching described in, for example, U.S. Pat. No. 6,876,796; optical filtering described in, for example, U.S. Pat. No. 7,092,591; wavelength filtering described in, for example, U.S. Pat. No. 7,062,131; lasers described in, for example, U.S. Pat. No. 6,741,628; light depolarization described in, for example, U.S. Pat. No. 6,891,998; and chemical and biological sensing described in, for example, U.S. Pat. No. 5,744,902.

Some known microresonator constructions involve placing a glass spherical microresonator in close proximity to an optical waveguide such as an optical fiber. In such cases, optical energy can transfer between the resonator and the optical waveguide by evanescent coupling. The separation between the resonator and the optical waveguide is typically less than one micron and must be controlled with precision to provide reproducible performance. Other forms of microresonators include disk- or ring-shaped microresonators described in, for example, U.S. Pat. No. 7,095,010.

SUMMARY OF THE INVENTION

Generally, the present invention relates to optical devices. The present invention also relates to optical sensors that include one or more microresonators.

In one embodiment, an optical microresonator system includes an optical waveguide and an optical microcavity that is optically coupled to the optical waveguide. The microcavity is capable of supporting primarily one or more resonant modes. The optical microresonator system further includes an optical microresonator that is optically coupled to the microcavity and is capable of supporting a resonant mode.

In another embodiment, an optical microresonator system includes a rectangular optical microcavity that has a thickness dimension h, a width dimension W, and a length dimension L. The optical microresonator system further includes an input optical waveguide that is optically coupled to the microcavity, and an optical microresonator that is optically coupled to the microcavity along a length of the microcavity. The ratio L/W is not greater than about 6.

In another embodiment, an optical sensor includes a microresonator system that is capable of supporting a first resonant mode and includes an optical microresonator and an optical microcavity that is capable of supporting primarily one or more resonant modes and is optically coupled to the optical microresonator. The microresonator system further includes a first optical waveguide that is optically coupled to the optical microcavity. The optical sensor further includes a light source that is in optical communication with the first optical waveguide and is capable of emitting light at a wavelength that corresponds to the first resonant mode of the microresonator system. The optical sensor further includes a detector that is in optical communication with the microresonator system. The detector is capable of detecting a characteristic of the first resonant mode. The characteristic of the first resonant mode changes when an analyte is brought near to the microresonator system. The detector can detect the change in the characteristic.

In another embodiment, an optical microresonator system includes a first optical waveguide and an optical microcavity that is optically coupled to the first optical waveguide and is capable of supporting primarily one or more resonant modes. The optical microresonator system further includes an optical Fabry Perot cavity that is optically coupled to the microcavity and is capable of supporting a resonant mode.

BRIEF DESCRIPTION OF DRAWINGS

The invention may be more completely understood and appreciated in consideration of the following detailed description of various embodiments of the invention in connection with the accompanying drawings, in which:

FIGS. 16A-16D are magnified views of different portions of the plot in FIG. 15.

In the specification, a same reference numeral used in multiple figures refers to the same or similar elements having the same or similar properties and functionalities.

DETAILED DESCRIPTION

Figure 1:
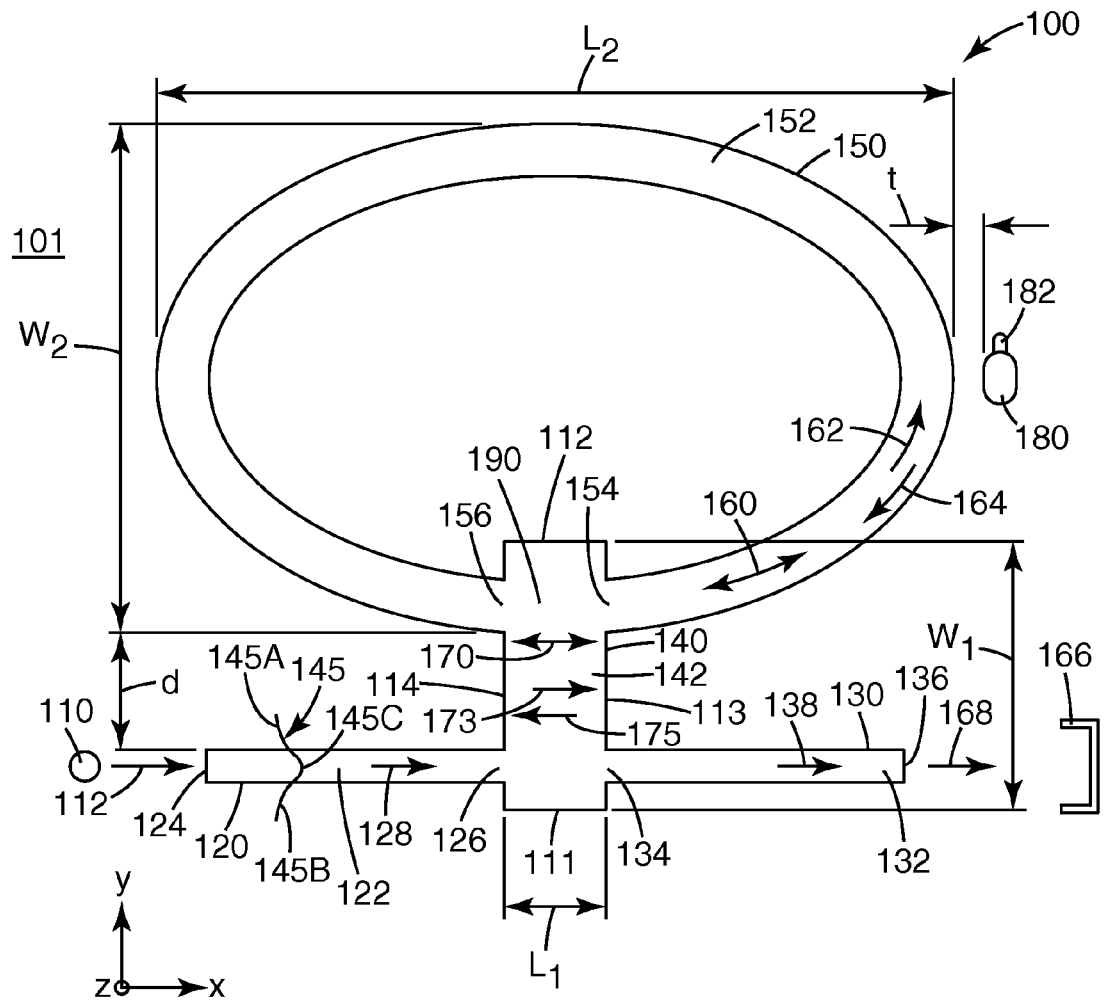
FIG. 1 is a schematic top-view of a microresonator system.

This invention generally relates to optical devices. The invention is particularly applicable to optical devices such as optical sensors, that incorporate microresonators.

The present application discloses optical devices that include one or more optical waveguides optically coupled to an optical microresonator via an optical microcavity. The optical microcavity is designed to primarily support one or more resonant, such as standing-wave, modes. For some disclosed optical devices, the performance of the optical device is relatively insensitive to the placement of the waveguide(s) and the microresonator relative to the microcavity. In such cases, the optical device can be manufactured at reduced costs since, for example, manufacturing errors and/or limitations in placing the optical waveguide(s) in optical proximity with the optical microcavity are less likely to result in a substantial change in the optical coupling and/or the device performance.

As used herein, for a given optical configuration such as an optical device disclosed in the present application, an optical mode refers to an allowed electromagnetic field in the optical configuration; radiation or radiation mode refers to an optical mode that is unconfined in the optical configuration; and a guided mode refers to an optical mode that is confined in the optical configuration in at least one dimension due to the presence of a high index region, where the high index region is typically a core region. A guided mode that is confined in one dimension (first dimension) may be referred to as a one-dimensional guided mode and a guided mode that is confined in two mutually orthogonal dimensions (first and second dimensions) may be referred to as a two-dimensional guided mode. A resonant mode refers to an optical mode that is confined in three mutually orthogonal dimensions (first, second, and third dimensions). A resonant mode may be considered a three-dimensional guided mode or a two-dimensional guided mode that is subject to an additional boundary condition requirement along a third dimension in the optical configuration, where the additional requirement is typically periodic in nature.

A resonant mode is a discrete mode resulting from a quantization of an optical mode in the optical configuration along three mutually orthogonal dimensions. In general, exciting or energizing an optical configuration at a frequency or wavelength corresponding to a resonant mode of the optical configuration results in a substantially stronger response by the optical configuration compared to a response resulting from an off-resonance excitation.

The mode profile of a resonant mode of an optical configuration is determined by boundary conditions along three mutually orthogonal dimensions. In some cases, a resonant mode can be a traveling-wave mode or substantially a traveling-wave mode. In some other cases, a resonant mode can be a standing-wave mode or substantially a standing-wave mode.

In some cases, a resonant mode can be capable of coupling to a radiation mode. In some other cases, a resonant mode can have a component that is radiation and not confined. In general, a guided mode can be a resonant or a non-resonant mode.

FIG. 1 shows a schematic top-view of a microresonator system 100. Microresonator system 100 includes a light source 110, a first optical waveguide 120, a second optical waveguide 130, an optical microcavity 140, an optical microresonator 150, and an optical detector 166.

First optical waveguide 120 includes an input face 124, an optical core 122, a cladding 101, and an output face 126. Optical waveguide 120 is capable of supporting a guided mode 128 that has an electric field profile 145. In general, for an electric field associated with a guided mode of waveguide 120, the evanescent tails of the field are located in the cladding regions of the waveguide and the peak(s) or maxima of the electric field are located in the core region of the waveguide. For example, guided mode 128 of waveguide 120 has evanescent tails 145A and 145B in cladding 101 and a peak 145C in core 122.

Second optical waveguide 130 includes an input face 134, an optical core 132, cladding 101, and an output face 136. Optical waveguide 130 is capable of supporting a guided mode 138.

Microcavity 140 includes an optical core 142 and cladding 101 and is optically coupled to waveguide 120 via contact point or output face 126. Similarly, microcavity 140 is optically coupled to second optical waveguide 130 via contact point or input face 134. Microcavity 140 is capable of supporting primarily one or more resonant modes where each resonant mode can be, for example, a traveling-wave, a standing-wave, or a combination of the two. In some cases, microcavity 140 may be capable of supporting a non-resonant mode such as a non-resonant traveling-wave, but such a non-resonant mode is secondary to the resonant modes that can be supported by the microcavity.

In some cases, a resonant mode of microcavity 140 can be primarily a standing-wave mode where, in general, the standing-wave can be equivalent to an interferometric superposition of two traveling-waves traveling in generally different such as opposite directions. In such cases, the resonant mode supported by microcavity 140 may have a resonant traveling portion, but any such traveling portion forms a small fraction of the overall resonant mode, meaning that the resonant mode is primarily standing-wave in nature and any resonant traveling portion of the mode is only secondary to the standing-wave portion of the mode.

In some cases, a resonant mode of microcavity 140 can be primarily a traveling-wave mode. In such cases, the resonant mode supported by microcavity 140 may have a resonant standing-wave portion, but any such standing-wave portion forms a small fraction of the overall resonant mode, meaning that the resonant mode is primarily traveling in nature and any resonant standing-wave portion of the mode is only secondary to the traveling portion of the mode.

A resonant mode of microcavity 140 can be primarily standing-wave in nature when, for example, the microcavity has a large reflection along a boundary of core 142 resulting in a large percentage of an incident wave being reflected as a reflected wave with the incident and reflected waves interfering to form a wave that is predominantly resonant in nature. Any traveling-wave component of the resonant mode is secondary to the standing-wave portion of the resonant mode.

A resonant mode of microcavity 140 can be primarily traveling in nature when, for example, the microcavity has a large reflection along a boundary of core 142 resulting in a large percentage of an incident wave being reflected as a reflected wave with the incident and reflected waves interfering to form a wave that is predominantly traveling-wave, in nature. Any standing-wave component of the resonant mode is secondary to the traveling-wave portion of the resonant mode.

Light source 110 is capable of emitting light beam 112, at least a portion of which enters first optical waveguide 120 through input face 124. In some cases, light entering optical waveguide 120 from light source 110 can propagate along the waveguide as a guided mode of the waveguide, such as guided mode 128. In some cases, guided mode 128 excites a resonant mode 170 of optical microcavity 140. In some cases, resonant mode 170 excites a resonant mode 160 of optical microresonator 150. In some cases, resonant modes 170 and 160 can be standing-wave modes of microcavity 140 and microresonator 150, respectively. In general, the optical coupling between resonant modes 170 and 160 can form a resonant mode of microresonator system 100.

In some cases, resonant mode 170 of microcavity 140 can excite guided mode 138 of second optical waveguide 130. Guided mode 138 can exit the second optical waveguide from output face 136 as an output light 168. Output light 168 can be detected by detector 166. In general, detector 166 is capable of detecting one or more characteristics of a mode, such as a resonant mode, of microresonator system 100 by detecting one or more characteristics of output light 168 such as intensity, wavelength, or phase.

In some cases, detector 166 can detect a change in a characteristic of output light 168, such as a change in wavelength or intensity. Such a change can indicate a change in microresonator system 100. A change in output light 168 can, for example, indicate a change in the refractive index of cladding 101 and/or a change in the refractive index of core 152 of microresonator 150. As another example, a change in output light 168 can, for example, indicate a dimensional change in microresonator system 100 due to, for example, a change in ambient temperature.

In some cases, a change in one or more characteristics of output light 168 can indicate the presence of an external agent, such as a scattering center 180 that can affect one or more characteristics of microresonator system 100. For example, if distance "t" between the scattering center and core 152 of optical microresonator 150 is sufficiently small, then the scattering center is sufficiently close to the microresonator to allow optical coupling between the microresonator and the scattering center. The optical coupling can change one or more characteristics of an excited resonant mode of microresonator system 100. For example, the optical coupling can change one or more characteristics of resonant mode 160 of microresonator 150. A change in mode 160 can lead to a change in one or more characteristics of guided mode 138 that exits second optical waveguide 130 as output light 168. Detector 166 can detect the change in mode 160 or the resonant mode of microresonator system 100 by detecting a corresponding change in output light 168.

In the exemplary microresonator system 100 shown in FIG. 1, scattering center 180 is proximate microresonator 150. In general, scattering center 180 can be sufficiently close to any part of microresonator system 100 that can lead to a change in a characteristic of a resonant mode of the microresonator system. For example, the scattering center may be sufficiently close to microcavity 140 to allow optical coupling between the scattering center and the microcavity.

A change in the strength of optical coupling between scattering center 180 and microresonator 150 can induce a change in a characteristic of, for example, resonant mode 160. The change in the strength of optical coupling can be achieved by various means. For example, a change in the spacing "t" between scattering center 180 and microresonator 150 or core 152 can change the strength of optical coupling between the scattering center and the microresonator. As another example, a change in the index of refraction $n_s$ of the scattering center can change the strength of optical coupling between the scattering center and the microresonator. In general, any mechanism that can cause a change in the strength of optical coupling between scattering center 180 and microresonator 150 can induce a change in a characteristic of output light 168 and a resonant mode of the microresonator system.

In some cases, such as in the case of some metals such as gold, the real part of the index of refraction of the scattering center is less than 1. In some other cases, such as in the case of silicon, the real part of the index of refraction of the scattering center is greater than 1 for wavelengths near 1550 nm.

Examples of scattering centers that can be used as scattering center 180 include silicon nanoparticles and metal nanoparticles, including gold and aluminum nanoparticles. In some cases, a scattering center may be a semiconductor such as Si, GaAs, InP, CdSe, or CdS. For example, a scattering center can be a silicon particle having a diameter of 80 nanometers and an index of refraction (the real part) of 3.5 for a wavelength of interest. Another example of a scattering center is a gold particle having a diameter of 80 nanometers and an index of refraction of 0.54+9.58i for wavelengths near 1550 nm. Another example of a scattering center is an aluminum particle having a diameter of 80 nanometers and an index of refraction of 1.44+16.0i for wavelengths near 1550 nm.

In some cases, the scattering center can be a dielectric particle. In some cases, the scattering center can be a non-fluorescent particle. In some cases, the scattering center is not a semiconductor.

In some cases, the size of scattering center 180 is no greater than about 1000 nanometers, or no greater than about 500 nanometers, or no greater than about 100 nanometers, or no greater than about 50 nanometers.

Microresonator system 100 can be used as a sensor, capable of sensing, for example, an analyte 182. For example, microresonator 150 may be capable of bonding with analyte 182. Such bonding capability may be achieved by, for example, a suitable treatment of the outer surface of microresonator 150 or core 152. In some cases, analyte 182 is associated with scattering center 180. Such an association can, for example, be achieved by attaching the analyte to the scattering center. The scattering center may be brought in optical proximity to microresonator 150 when analyte 182 bonds with the outer surface of the microresonator. The scattering center induces a change in a characteristic of resonant mode 160 which, in turn, results in a change in a characteristic of a resonant mode of the microresonator system. Optical detector 166 can detect the presence of analyte 182 by detecting the change in the characteristic of resonant mode 160 by monitoring changes in one or more characteristics of output light 168. In some cases, the induced change can be a frequency shift in mode 160. In such cases, optical detector 166 can detect the frequency shift. Analyte 182 can, for example, include a protein, a virus, or a DNA.

In some cases, analyte 182 can include a first antibody of an antigen that is to be detected. The first antibody can be associated with scattering center 180. A second antibody of the antigen can be associated with microresonator 150. The antigen facilitates a bonding between the first and second antibodies. As a result, the scattering center is brought into optical contact with the microresonator and induces a change in a characteristic of a resonant mode present in the microresonator system. The detector can detect the presence of the scattering center, and therefore the antigen, by detecting the change in the characteristic. In some cases, the first antibody can be the same as the second antibody. Such an exemplary sensing process can be used in a variety of applications such as in food safety, food processing, medical testing, environmental testing, and industrial hygiene. In some cases, scattering center 180 can induce a frequency shift in resonant mode 160 and thereby in a corresponding resonant mode of the microresonator system, where the shift can be detected by detector 166.

In some cases, microresonator system 100 can be capable of detecting a change in the index of refraction of cladding layer 101. For example, cladding layer 101 may initially be air. With an air cladding, a resonant mode of the microresonator system can be at a resonant frequency $f_1$ which can result in an output light 168 at the resonant frequency $f_1$. A change in the index of refraction of cladding layer 101 can occur when, for example, the air cladding is replaced by or mixed with, for example, a vapor, such as an organic vapor, a gas, a liquid, a biological or chemical material, or any other material that can result in a change in the index of refraction of cladding 101. The change in the index of refraction of cladding 101 can result in the resonant mode of the microresonator system and output light 168 shifting to a frequency $f_2$ where $f_2$ is different than $f_1$. Optical detector 166 can detect the frequency shift $\Delta f = f_1 - f_2$.

Figure 2:
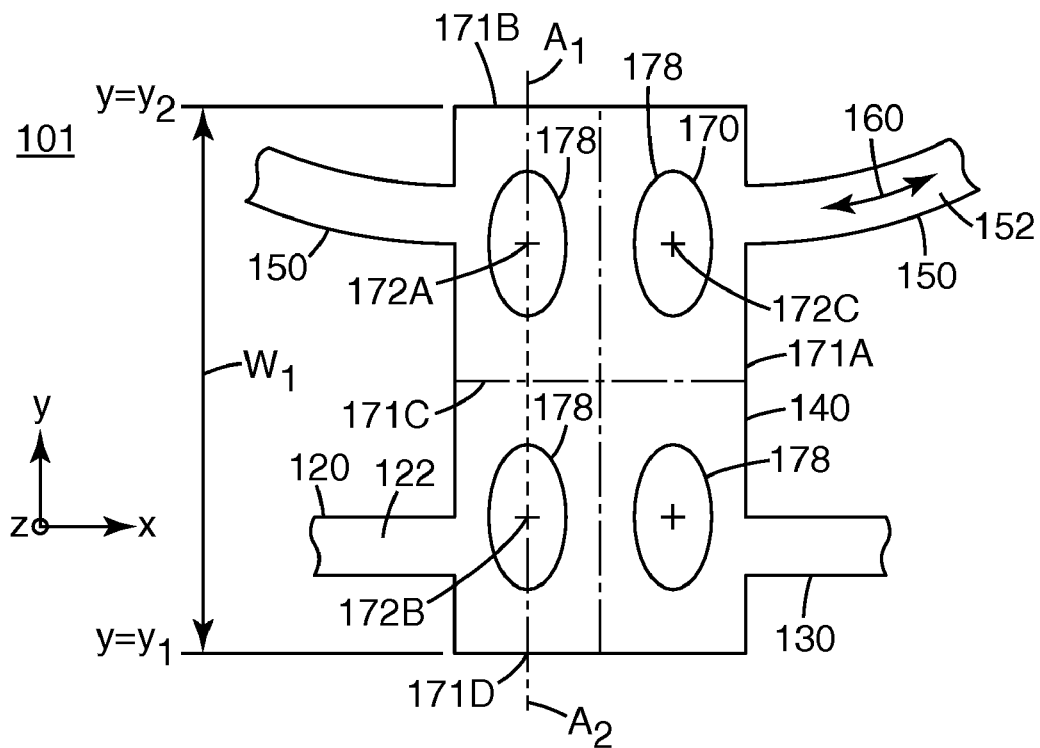
FIG. 2 is a magnified view of a portion of the microresonator system in FIG. 1.

FIG. 2 shows a magnified portion of microresonator system 100. Microcavity 140 supports a resonant standing-wave mode 170 resulting from the interference between two or more traveling-wave modes traveling in different, for example opposite, directions. Mode 170 includes a plurality of node-lines, such as node-lines 171A-171C along the outer surface of the core of the microcavity and node-line 171C within the microresonator core, resulting from destructive interference between the traveling-wave modes. A node on a node-line is generally a point on mode 170 at a minimum field amplitude of the mode. Typically, the mode undergoes minimum or no oscillation at a node. In some cases, the mode amplitude can be zero or close to zero at a node. In some cases, a node may be a traveling node. In some other cases, a node may be substantially non-traveling or still with time. A node in a standing-wave mode is a substantially stationary point when, for example, the standing-wave mode results from the interference of two otherwise substantially identical traveling-wave modes that travel in opposite directions.

Standing-wave mode 170 further includes a plurality of antinodes, such as antinodes 172A-172C, located at points of maximum constructive interference between the traveling-wave modes that form the standing-wave mode. An antinode is generally a point on the standing-wave mode at a peak or maximum of the standing-wave mode. An antinode typically oscillates between a maximum positive field strength and a maximum negative field strength. In some cases, an antinode may be a traveling antinode. In some other cases, an antinode may be substantially still with time. An antinode in a standing-wave mode is substantially stationary when, for example, the standing-wave mode results from the interference of two otherwise substantially identical traveling-wave modes traveling in opposite directions. Lines 178 represent exemplary contours of constant field intensity.

Figure 3:
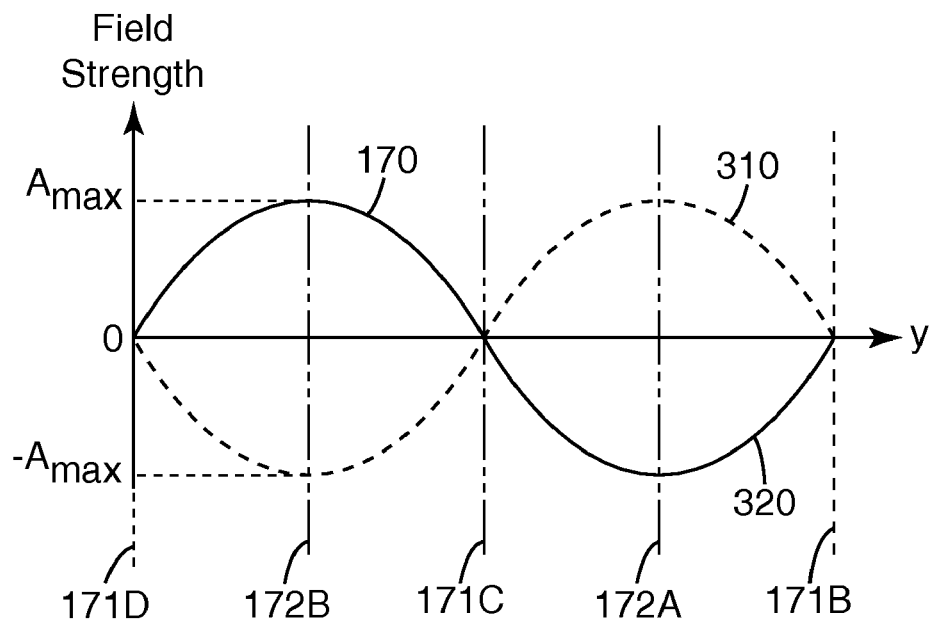
FIG. 3 is a schematic profile of a standing-wave.

FIG. 3 shows a schematic cross-sectional profile of standing-wave mode 170 in the yz-plane along direction $A_1A_2$. Standing-wave mode 170 oscillates between a first envelope 310 and a second envelope 320. In the exemplary profile shown in FIG. 3, the node at 171C has zero amplitude. In general, the node at 171C may or many not have a zero amplitude.

In the exemplary standing-wave mode 170 shown in FIG. 3, nodes 171C-171E are located at points of zero field strength. In general, a node of a standing-wave mode may or may not have a zero strength. Antinodes 172A and 172B oscillate between a positive maximum field strength $A_{max}$ and a negative maximum field strength $-A_{max}$.

The exemplary standing-wave mode 170 shown in FIG. 2 has two antinodes along the y-direction and two anti-nodes along the x-direction. In general, a standing-wave mode of microcavity 140 may have one or more antinodes along the x-direction and one or more antinodes along the y-direction.

A resonant standing-wave mode of microcavity 140 can be denoted as $\Psi_{m,n}$ where m refers to the number of antinodes of the mode along the x-axis and n refers to the number of antinodes of the mode along the y-axis. For example, standing-wave mode 170 can symbolically be represented as $\Psi_{2,2}$ having two antinodes in each of x- and y-directions.

Figure 4A:
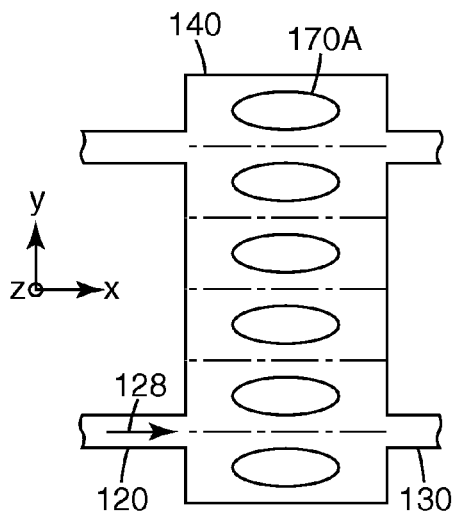
FIGS. 4A-4E are schematic representations of various standing-wave modes in a microcavity.
Figure 4B:
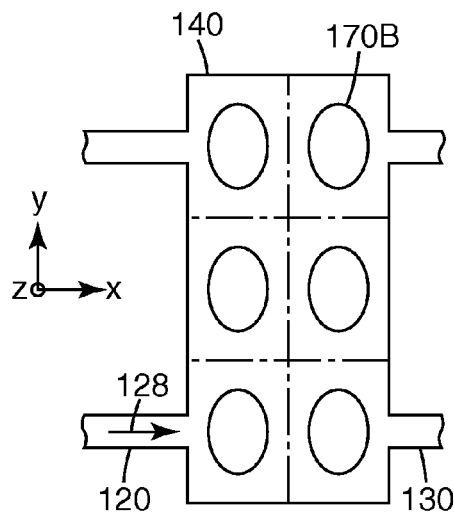
Figure 4C:
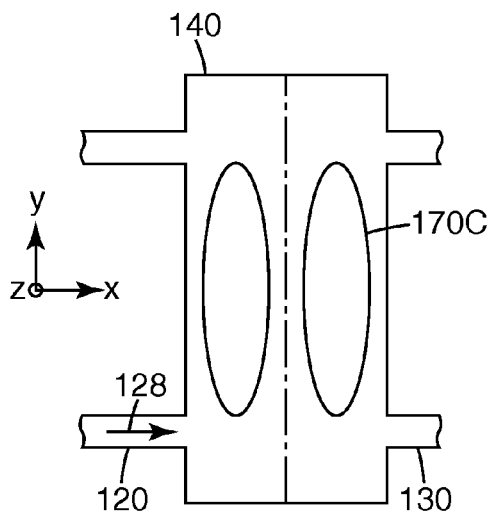
Figure 4D:
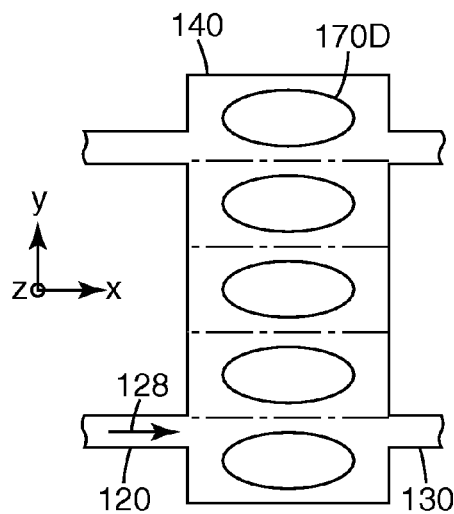
Figure 4E:
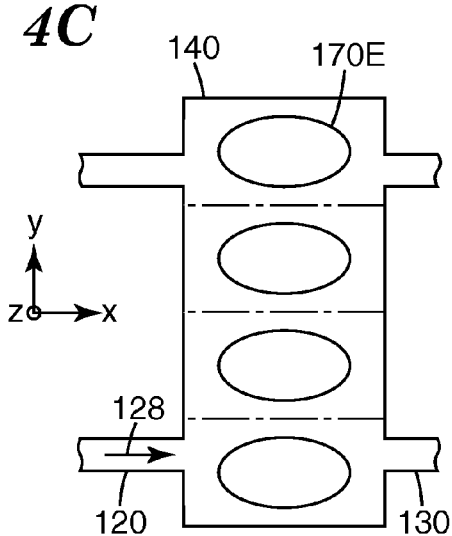

Some exemplary standing-wave modes of microcavity 140 are schematically shown in FIGS. 4A-4E. In particular, FIG. 4A shows a standing-wave mode 170A denoted symbolically as $\Psi_{1,6}$ having one antinode along the x-axis and 6 antinodes along the y-axis, FIG. 4B shows a standing-wave mode 170B denoted symbolically as $\Psi_{2,3}$ having 2 antinodes along the x-axis and 3 antinodes along the y-axis, FIG. 4C shows a standing-wave mode 170C denoted symbolically as $\Psi_{2,1}$ having two antinodes along the x-axis and one antinode along the y-axis, FIG. 4D shows a standing-wave mode 170D denoted symbolically as $\Psi_{1,5}$ having one antinode along the x-axis and 5 antinodes along the y-axis, and FIG. 4E shows a standing-wave mode 170E denoted symbolically as $\Psi_{1,4}$ having one antinode along the x-axis and 4 antinodes along the y-axis.

Guided mode 128 of first optical waveguide 120 is capable of coupling to optical microcavity 140 via a coupling region at or near output face 126. As a result, guided mode 128 is capable of exciting a resonant mode, such as resonant mode 170, of the microcavity at the same frequency and/or wavelength where the wavelength can be, for example, the free space wavelength. In some cases, for a given wavelength, guided mode 128 is capable of exciting primarily one resonant mode of microcavity 140, or primarily two resonant modes of microcavity 140, or primarily three resonant modes of microcavity 140. For example, where guided mode 128 excites primarily two resonant modes of microcavity 140, any other resonant and/or non-resonant modes excited by the guided mode are only secondary in mode characteristics, such as mode optical power or intensity, to the two primary excited resonant modes.

In some cases, guided mode 128 is capable of primarily exciting one of resonant modes 170 and 170A-170E. For example, in some cases, guided mode 128 may primarily excite resonant mode 170A. In such cases, guided mode 128 may also excite mode 170B, but mode 170A will be the primary resonant mode present in microcavity 140 and resonant mode 170B will be, for example, substantially of lower intensity than mode 170A. In some cases, modes 170A and 170B can have the same or substantially the same frequency and/or wavelength.

In some cases, guided mode 128 may excite primarily one or more resonant modes, such as mode 170A, of microcavity 140 and to a much lesser extent one or more non-resonant modes of microcavity 140. In such cases, most of the optical energy from guided mode 128 that is coupled to the excited modes of the microcavity is coupled to the resonant modes of the microcavity.

In the case of resonant standing-wave modes, in some cases, guided mode 128 may excite primarily one or more standing-wave modes, such as mode 170A, of microcavity 140 and to a much lesser extent one or more traveling-wave modes of microcavity 140. In such cases, most of the optical energy from guided mode 128 that is coupled to the excited modes of the microcavity is coupled to the standing-wave modes of the microcavity.

In some cases, guided mode 128 at different wavelengths may primarily excite different resonant modes of microcavity 140. For example, guided mode 128 having a first wavelength $\lambda_1$ can primarily excite resonant mode 170A, while the guided mode having a second wavelength $\lambda 2$ can primarily excite a different resonant mode such as resonant mode 170C.

In some cases, microcavity 140 may be capable of supporting degenerate resonant modes, meaning that guided mode 128 having a wavelength 3 can excite primarily two or more resonant modes, such as modes 170A and 170B, having the same wavelength $\lambda_3$. In some cases, microcavity 140 may be capable of supporting degenerate resonant modes, such as resonant standing-wave modes, for one ratio $L_1/W_1$ but not for another ratio. In some cases, microcavity 140 may be capable of supporting degenerate resonant modes for one or more discrete ratios $L_1/W_1$.

Optical microresonator 150 includes an optical core 152 and cladding 101 and is optically coupled to optical microcavity 140 via first face 154 and second face 156. Optical microresonator 150 is capable of supporting a resonant mode 160. In some cases, resonant mode 160 can be a traveling-wave mode propagating around microresonator 150 and satisfying the round trip condition(s) for resonance. For example, the phase of a resonant traveling-wave mode 160 traveling a round trip around the microresonator changes by an integer multiple of 2π.

In some cases, resonant mode 160 can be a standing-wave mode of optical microresonator 150. In such cases, resonant standing-wave mode 160 can include counter propagating first and second traveling-wave optical modes 162 and 164, respectively. Standing-wave mode 160 and traveling-wave optical modes 162 and 164 have the same frequency and/or wavelength.

In some cases, at least one of first and second traveling-wave modes 162 and 164 can be a traveling guided mode of microresonator 150. For example, first and second guided optical modes 162 and 164 may be "whispering gallery modes" (WGMs) of microresonator 150. A WGM is generally a traveling mode confined close to the surface of a microresonator cavity and has relatively low radiation loss. Since the WGMs are confined near the outer surface of the core of a microresonator, they are well-suited to optical coupling with analytes on or near the microresonator surface.

In some cases, a resonant mode of microcavity 140 is capable of exciting a resonant mode of microresonator 150. In some cases, a standing-wave mode of microcavity 140 is capable of exciting a standing-wave mode of microresonator 150. For example, standing-wave mode 170 of the microcavity can optically couple to and excite standing-wave mode 160 of the microresonator.

In some cases, standing-wave mode 170 results from optical interference between two traveling-wave modes traveling in different directions, such as first traveling-wave mode 173 and second traveling-wave mode 175. In some cases, traveling-wave mode 173 can optically couple to and excite primarily traveling-wave mode 162 and traveling-wave mode 175 can optically couple to and excite primarily traveling-wave mode 164. In such cases, excited traveling-wave modes 162 and 164 can optically interfere to form standing-wave mode 160.

In FIG. 1, traveling modes 173 and 175 are schematically shown to be traveling along the x-direction. In general, each of modes 173 and 175 can travel along any direction. For example, each of modes 173 and 175 can have a wave vector with varying direction and, for example, constant magnitude. In some cases, the horizontal arrows representing modes 173 and 175 in FIG. 1 can represent the x-components of the wave vectors associated with the two modes.

In the exemplary microresonator system 100, each of cores 122, 132, and 152 extend from core 142 of the microcavity. As a result, optical coupling between microcavity 140 and each of optical waveguides 120 and 130 is primarily a core coupling and not an evanescent coupling. Similarly, the optical couplings between microcavity 140 and microresonator 150 at faces 154 and 156 are primarily core couplings.

In some cases, cores 122, 132, 142, and 152 may be made of different core materials having the same or different indices of refraction. In some other cases, cores 122, 132, 142, and 152 may form a unitary construction, meaning that the cores form a single unit with no physical interfaces between connecting cores. In a unitary construction, the cores are typically made of the same core material. A unitary construction can be made using a variety of known methods such as etching, casting, molding, embossing, and extrusion.

In the exemplary microresonator system 100, microresonator 150 optically couples to optical waveguides 120 and 130 via microcavity 140 where the optical coupling between each waveguide and the microcavity is by core coupling, and the optical coupling between the microresonator and the microcavity is also by core coupling.

In general, an optical coupling in microresonator system 100 may be by evanescent or core coupling. For example, in some cases, at least one of optical waveguides 120, 130, and microresonator 150 may optically couple to microcavity 140 by evanescent coupling.

A characteristic of core coupling is elimination of a coupling gap. In known microresonators, a gap exists between an optical waveguide and, for example, a microresonator. In such cases, the optical coupling between the waveguide and the microresonator is achieved by evanescent coupling. Such a coupling is very sensitive to, among other things, the size of the coupling gap which is typically hard to reproducibly control because of, for example, fabrication errors. Even in fabrication methods where the gap can be controlled with sufficient accuracy, such a control can significantly increase the manufacturing cost. In some exemplary embodiments disclosed in the present application, the coupling gap between an optical waveguide and the microcavity is eliminated by providing direct physical contact between their respective cores. Similarly, in some exemplary embodiments, the coupling gap between the microresonator and the microcavity is eliminated by providing one or more direct physical contacts between their respective cores. The elimination of a coupling gap can result in reduced manufacturing cost and improved reproducibility.

Figure 5A:
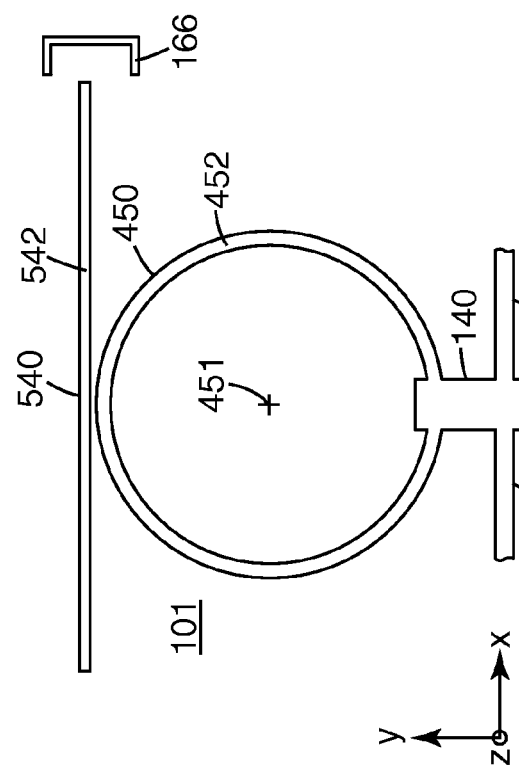
FIGS. 5A and 5B are schematic top-views of two microresonator systems.

Microresonator 150 of FIG. 1 is shown to be an oval or elliptical ring microresonator. In general, microresonator 110 can be any type microresonator, such as any shape microresonator, capable of supporting at least one resonant mode and capable of optically coupling to microcavity 140. In some cases, microresonator 150 has a circular symmetry, meaning that the perimeter of a cross-section of core 152 of microresonator 150 can be expressed as a function of distance from a central point only. In some cases, such as in a circular ring microresonator 450 shown schematically in FIG. 5A, the central point can be center 451 of core 452 of the microresonator. Other exemplary microresonator shapes having circular symmetry include a sphere, a disk, and a cylinder.

In some cases, microresonator 150 can have spherical symmetry such as in the case of a sphere-shaped microresonator. In some cases, microresonator 150 can be a closed loop microresonator such as a racetrack microresonator 460 shown schematically in FIG. 5B. Core 462 of microresonator 460 has linear portions 430, 432, and 434 and curved portions 436 and 438.

In general, microresonator 150 may be single or multimode along a particular direction. For example, microresonator 150 can be single mode or multimode along the thickness direction (e.g., the z-direction) of the microresonator. In some cases, such as in the case of a ring-shaped microresonator, the microresonator can be single or multimode along a radial direction. In some cases, such as in the case of a ring-shaped microresonator, traveling-wave guided modes 162 and 164 of microresonator 150 can be azimuthal modes of the microresonator.

Optical waveguides 120 and 130 can be any type of waveguide capable of supporting an optical guided mode. Optical waveguides 120 and 130 can be one-dimensional waveguides such as planar waveguides, where a one-dimensional waveguide refers to light confinement along one direction. In some cases, optical waveguides 120 and 130 can be two-dimensional waveguides, where a two-dimensional waveguide refers to light confinement along two mutually orthogonal directions. Exemplary two-dimensional optical waveguides include a channel waveguide, a strip loaded waveguide, a rib or ridge waveguide, and an ion-exchanged waveguide.

In the exemplary microresonator system 100, core 122 of first optical waveguide 120 and core 132 of second optical waveguide 130 are substantially parallel at or near their respective contact points with microcavity 140. In particular, both cores 122 and 132 extend along the x-axis at contact points 126 and 134, respectively. In addition, cores 122 and 132 are collinear. In general, cores 122 and 132 may or may not be parallel at their respective contact points with microcavity 140. Similarly, cores 122 and 132 may or may not be collinear at their respective contact points with microcavity 140.

In the exemplary microresonator system 100 shown in FIG. 1, optical microcavity 140 is a rectangular solid having a length $L_1$ along the x-axis and a width $W_1$ along the y-axis. In general, microcavity 140 can be any optical microcavity capable of supporting primarily one or more resonant modes. Exemplary shapes for optical microcavity 140 include a sphere, a disk, a cylinder, a ring, a toroid, and a racetrack. In some cases, microcavity 140 can be a closed loop microcavity.

In some cases, width sides 113 and 114 of optical microcavity 140 are sufficiently reflective so that the allowed optical modes of the microcavity are quantized into discrete modes along the x-axis. In general, a mode of microcavity 140 undergoes a strong reflection at an interface between a cladding and the microresonator when the effective index associated with the mode is different, for example sufficiently different, than the effective cladding index at the interface. For example, a width side, such as width side 113 or 114, can be sufficiently reflective if, for example, the effective index of a mode supported by microcavity 140 is different than the effective index of a mode supported by, for example, optical microresonator 150 or optical waveguide 130. In some cases, length sides 111 and 112 of optical microcavity 140 are sufficiently reflective so that the allowed optical modes of the microcavity are quantized into discrete modes along the y-axis.

In general, optical microresonator 150 is optically coupled to microcavity 140 in a coupling region 190 that includes faces 154 and 156. In general, a coupling region between two waveguides is the region, such as the space, where optical coupling occurs between the two waveguides. The separation between microresonator core 152 and core 122 of waveguide 120 is d where d is less than $W_1$.

Figure 6:
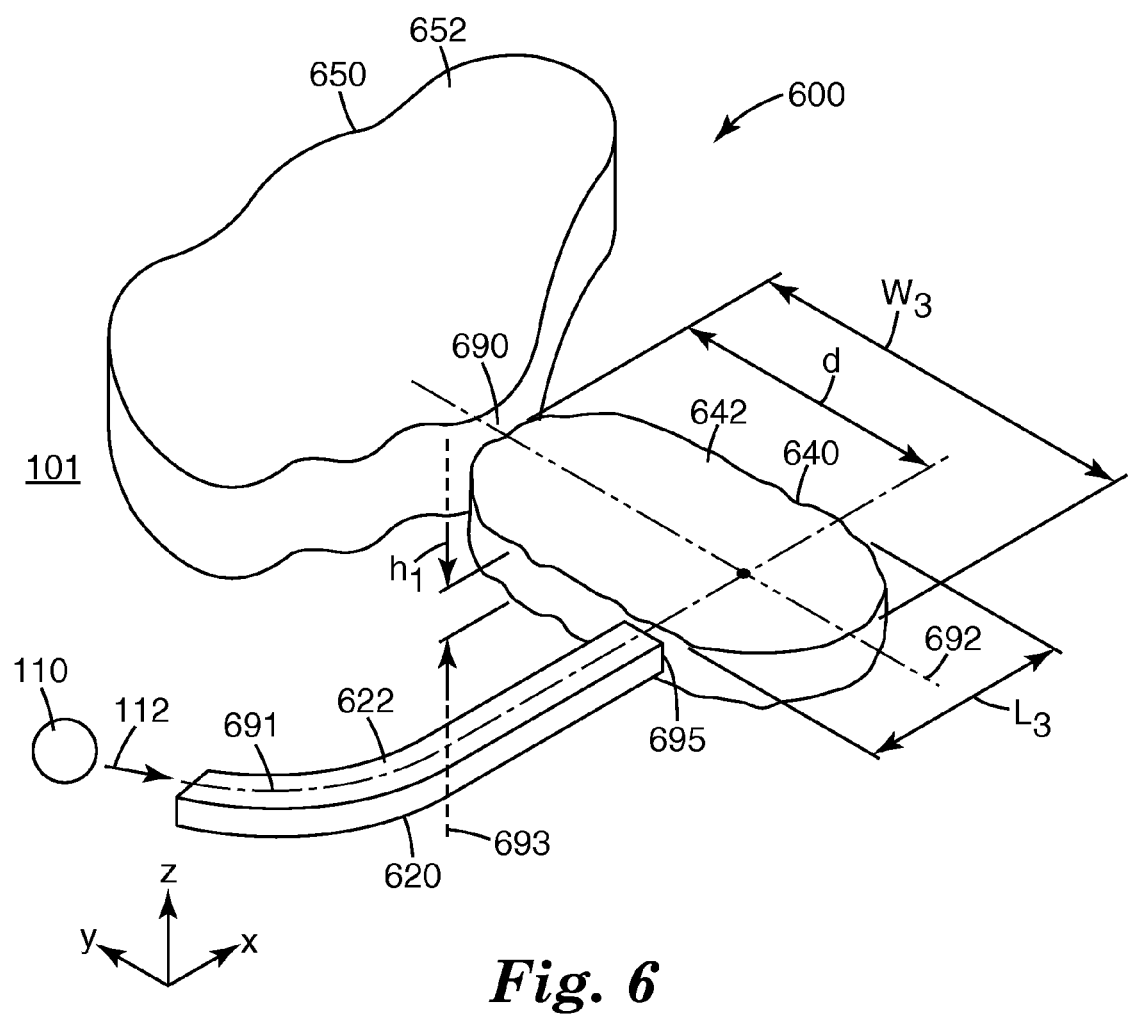
FIG. 6 is a schematic three-dimensional view of a microresonator system.

FIG. 6 shows a schematic three-dimensional microresonator system 600 that includes an optical microresonator 650 that includes a core 652, is capable of supporting a resonant mode, and is optically coupled in a coupling region 690 to an optical microcavity 640. Coupling region 690 defines an optical gap between the microresonator and the microcavity.

Microresonator system 600 also includes an optical waveguide 620 centered on an optical axis 691. Optical waveguide 620 includes a core 622 that extends from a core 642 of the microcavity, thereby defining a coupling region 695 between the microcavity and the waveguide.

In the exemplary microresonator system shown in FIG. 6, the optical coupling between the microresonator and the microcavity is by evanescent coupling and the optical coupling between the waveguide and the microcavity is a core coupling.

In the exemplary microresonator system 600, the distance between microresonator core 652 and optical waveguide core 622 at coupling region 690 is d, where d is determined by extending optical axis 691 beyond coupling region 695 and drawing a line 692 normal to the optical axis from coupling region 690. Direction 692 is along the y-axis although, in general, direction 692 can be along a different direction. Microcavity 640 has a largest dimension $W_3$ along direction 692.

Microcavity 640 has a largest thickness $h_1$ along a direction 693 orthogonal to direction 692. In the exemplary embodiment of FIG. 6, direction 693 is along the z-axis. Microcavity 640 has a largest dimension $L_3$ along a direction, in this case the x-axis, orthogonal to directions 692 (the y-axis) and 693 (the z-axis).

Figure 7:
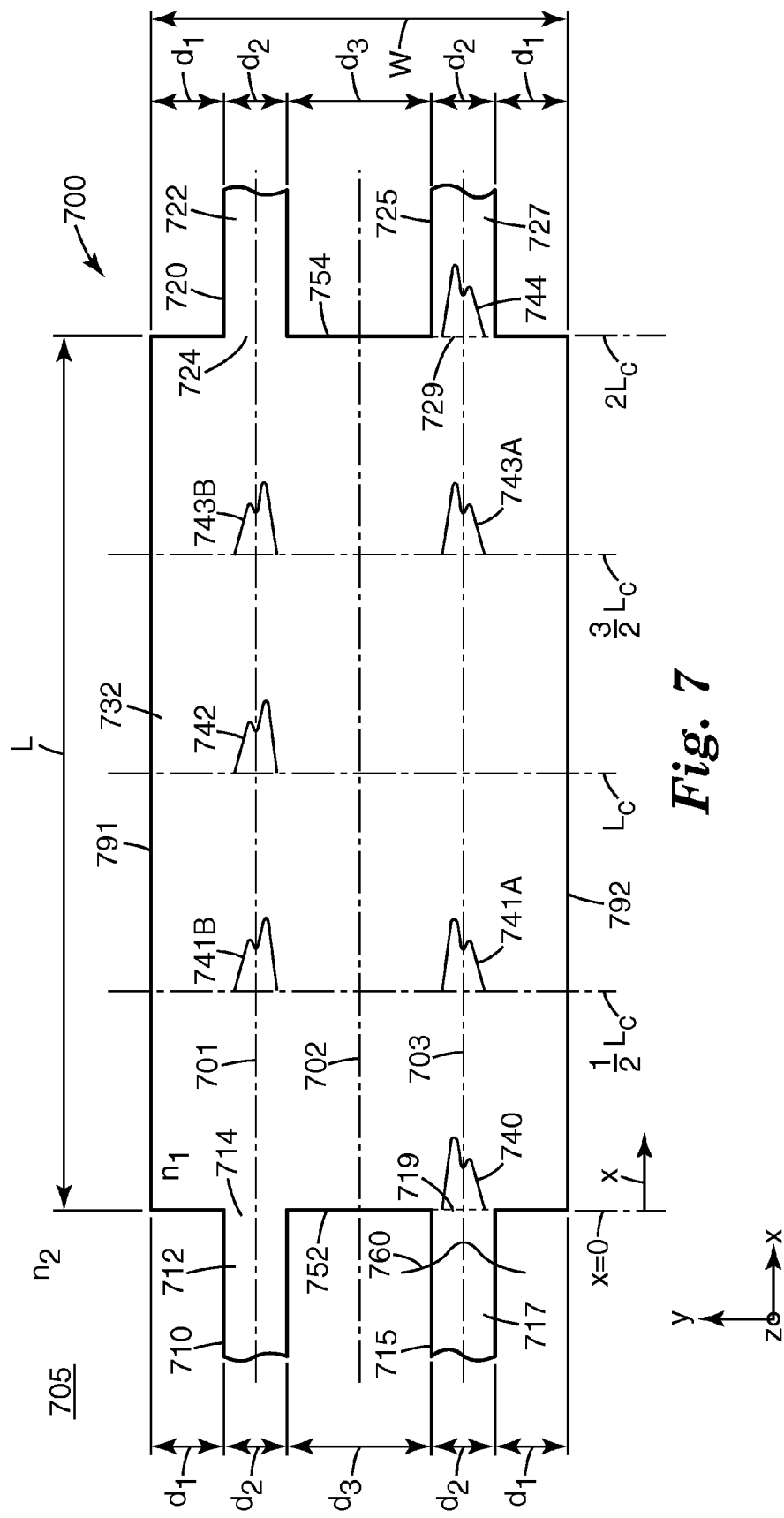
FIG. 7 is a schematic top-view of a multimode interference coupler.

FIG. 7 shows a schematic top-view of an optical multimode interference coupler (MMIC) 700 described in, for example, Soldano et al., "*Optical Multi-Mode Interference Devices Based on Self-Imaging: Principles and Applications*", Journal of Lightwave Technology 13(4), pp. 615-626, April 1995. MMIC 700 is centered on an optical axis 702 along the x-axis and includes a rectangular optical cavity 730 and two-dimensional optical waveguides 710, 715, 720, and 725. Optical cavity 730 has a core 732, a cladding 705, a first input port 714, a second input port 719, a first output port 724, and a second output port 729. Optical cavity 730 has a length L along the x-axis and a width W along the y-axis.

Optical waveguide 710 is centered on an optical axis 701 and has a core 712, cladding 705, and is optically core coupled to cavity 730 at first input port 714; optical waveguide 715 is centered on an optical axis 703 and has a core 717, cladding 705, and is optically core coupled to cavity 730 at second input port 719; optical waveguide 720 is centered on optical axis 701 and has a core 722, cladding 705, and is optically core coupled to cavity 730 at first output port 724; and optical waveguide 725 is centered on optical axis 703 and has a core 727, cladding 705, and is optically core coupled to cavity 730 at second output port 729. Input ports 714 and 719 are associated with input side or width side 752 of optical cavity 730, and output ports 724 and 729 are associated with output side or width side 754 of the optical cavity.

Each optical waveguide in MMIC 700 has a core width $d_2$ and is separated by a distance $d_1$ from the nearest length side of optical cavity core 732. Optical waveguides 710 and 715 are separated by a distance $d_3$ equal to $W-2(d_1+d_2)$. Optical waveguides 720 and 725 are also separated by the distance $d_3$.

For simplicity and without loss of generality it is assumed that the cavity and the four waveguides have the same cladding 705 having an index $n_2$. It is further assumed that the cores of the four waveguides and the optical cavity have the same index $n_1$.

Length sides 791 and 792 of cavity core 732 are sufficiently reflective and width sides 752 and 754 of core 732 are sufficiently transmissive for a wavelength of interest so that the allowed optical modes of cavity 730 are quantized into discrete modes along the y-axis but not along the x-axis. Each of width sides 752 and 754 can be sufficiently optically transmissive by having the same or substantially the same modal effective index on both sides of the width.

Since width sides 752 and 754 are not sufficiently reflective, optical cavity 730 is capable of supporting primarily non-resonant modes, such as non-resonant guided modes, traveling along the x-direction. The MMIC is designed so that light launched in, for example, second input waveguide 715, excites a plurality of non-resonant traveling-wave modes in optical cavity 730 at input side 752. The plurality of non-resonant traveling waves travel along the x-axis and interfere in such a way at output side 754 so that substantially all light in the optical cavity exits the cavity and enters output waveguides 720 and/or 725 through output ports 724 and 729, respectively. Therefore, optical cavity 730 is not capable of primarily supporting resonant modes because the MMIC is so designed that no portions or at most very small portions of the plurality of traveling-wave modes are reflected at, for example, output side 754 of optical cavity 730.

In some cases, a small fraction of a traveling-wave mode of optical cavity 730 traveling along the x-axis from input side 752 and incident on output side 754 may be reflected at the output side. The reflection, however, is so small that any optical interference between the incident and reflected waves results in a mode that is primarily a non-resonant mode. For example, the reflection at the output side is so small that any optical interference between the incident and reflected waves results in a mode that is primarily a non-resonant traveling-wave mode and not a resonant standing-wave mode.

An optical guided mode 760 in second input waveguide is capable of exciting a traveling-wave electric field $\Phi(x,y)$ within optical cavity 730 that can have a varying profile along the y-axis as a function of x, where for simplicity and without loss of generality it is assumed that x=0 corresponds to input side 752. For example, field $\Phi(0,y)$ has a field profile 740 substantially centered on optical axis 703 as shown schematically in FIG. 7. It will be appreciated that the particular field profile 740 shown in FIG. 7 is meant to be illustrative and not limiting. Accordingly, the disclosed embodiments should not be construed as limited to any particular field profile.

Figure 8:
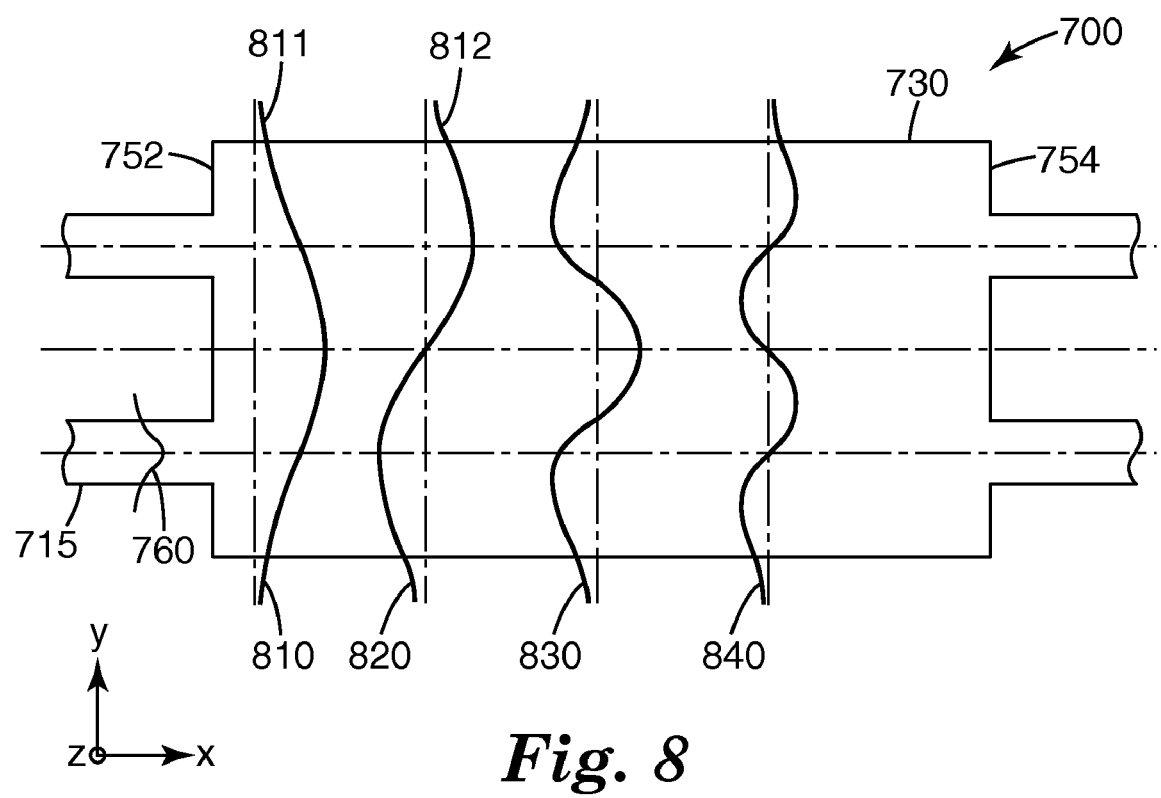
FIG. 8 is a schematic representation of exemplary guided modes of an optical cavity.

Assuming for simplicity and without loss of generality that field $\Phi(x,y)$ includes no unguided, such as radiation, modes, traveling field $\Phi(x,y)$ can be expressed as a linear combination of optical guided modes of optical cavity 730 as described in, for example, Soldano et al., "*Optical Multi-Mode Interference Devices Based on Self-Imaging: Principles and Applications*", Journal of Lightwave Technology 13(4), pp. 615-626, April 1995. Some examples of guided modes of the optical cavity are schematically shown in FIG. 8, such as zeroth order guided mode 810 having a single peak, first order guided mode 820 having two peaks, second order guided mode 830 having three peaks, and third order guided mode 840 having four peaks.

Optical cavity 730 has a characteristic length $L_c$ associated with a mode supported by the cavity that is given below in Equation 1:

$$L_c = \frac{4n_1 W_e^2}{\lambda_o} \qquad \text{(Equation 1)}$$

where $n_1$ is the refractive index of core 732, $\lambda_o$ is the wavelength in free space, and $W_e$ is the effective width of optical cavity 730 for the supported mode. Effective width $W_e$ accounts for mode evanescent tails, such as tails 811 and 812, and can be different from width $W_1$ of optical cavity 730.

Traveling field $\Phi(x,y)$ varies periodically along the x-axis. For example, at $x=(1/2)L_c$ traveling field $\Phi((1/2)L_c,y)$ includes a traveling field 741A that resembles field 740 and is substantially centered on optical axis 703, and a traveling field 741B that is substantially a mirror image of field 741A and is substantially centered on optical axis 701 as shown schematically in FIG. 7. In cases where length L of optical cavity 730 is equal to $(1/2)L_c$, field 741A is capable of substantially coupling to a guided mode of second output waveguide 725 at second output port 729 and field 741B is capable of substantially coupling to a guided mode of first output waveguide 720 at first output port 724. In such cases, about 50% of light from guided mode 760 transfers to second output waveguide 725 and about 50% of light from guided mode 760 transfers to first output waveguide 720. Accordingly, for $L=(1/2)L_c$, MMIC coupler 700 can be referred to as a 50:50 coupler.

As another example, at $x=L_c$ traveling field $\Phi(L_c,y)$ includes a traveling field 742 that resembles a mirror image of field 740 and is substantially centered on optical axis 701 as shown schematically in FIG. 7. In cases where length L of optical cavity 730 is equal to $L_c$, field 742 is capable of substantially coupling to a guided mode of first output waveguide 720 at first output port 724. In such cases, about 100% of light from guided mode 760 transfers to first output waveguide 720 and about 0% of light from guided mode 760 transfers to second output waveguide 725. Accordingly, for $L=L_c$, MMIC coupler 700 can be referred to as a 0:100 coupler.

As another example, at $x=(3/2)L_c$ traveling field $\Phi((3/2)L_c,y)$ substantially resembles traveling field $\Phi((1/2)L_c,y)$. Accordingly, for $L=(3/2)L_c$, MMIC coupler 700 is a 50:50 coupler.

As yet another example, at $x=2L_c$ traveling field $\Phi(2L_c,y)$ includes a traveling field 744 within optical cavity 730 that resembles field 740 and is substantially centered on optical axis 703 as shown schematically in FIG. 7. In cases where length L of optical cavity 730 is equal to $2L_c$, field 744 is capable of substantially coupling to a guided mode of second output waveguide 725 at second output port 729. In such cases, about 100% of light from guided mode 760 transfers to second output waveguide 725 and about 0% of light from guided mode 760 transfers to first output waveguide 720. Accordingly, for $L=2L_c$, MMIC coupler 700 can be referred to as a 100:0 coupler.

Therefore, the minimum length $L_{50:50}$ for a 50:50 MMIC 700 is given in Equation 2:

$$\frac{L_{50:50}}{W_e} = \frac{2n_1 W_e}{\lambda_o}, \qquad \text{(Equation 2)}$$

and the minimum length $L_{0:100}$ for a 0:100 MMIC 700 is given below in Equation 3:

$$\frac{L_{0:100}}{W_e} = 2\left(\frac{2n_1 W_e}{\lambda_o}\right), \qquad \text{(Equation 3)}$$

Assuming for simplicity and without loss of generality that optical cavity 730 is a single mode cavity in the z-direction, then the optical cavity can support at least m modes along the y-direction if, as described in, for example, P. Yeh, et al., *Optical Waves in Layered Media*, John Wiley and Sons, New York (1988), the following relationship is satisfied:

$$W_e > m\frac{\lambda_o}{2n_1} \qquad \text{(Equation 4)}$$

Therefore, the minimum length $L_{50:50}$ for a 50:50 MMIC 700 is given by the expression:

$$\frac{L_{50:50}}{W_e} > m \qquad \text{(Equation 5)}$$

and the minimum length $L_{0:100}$ for a 0:100 MMIC 700 is given by the expression:

$$\frac{L_{0:100}}{W_e} > 2m \qquad \text{(Equation 6)}$$

Since effective width $W_e$ is generally greater than W, Equations (5) and (6) still hold when $W_e$ is replaced with W. In general, core index $n_1$ can be in a range from about 1.5 to about 3.5 and cladding index $n_2$ can be in a range from about 1.44 to about 1.51. For such ranges of $n_1$ and $n_2$, the effective width $W_e$ is no more than about 10% greater than W.

In a multimode interference coupler, optical cavity 730 must be a multimode cavity in the y-direction capable of supporting at least two traveling-wave guided modes ($m \geq 2$), such as guided modes 810 and 820 shown in FIG. 8. Accordingly, for a 50:50 coupler, the ratio L/W must be greater than 2 and for a 0:100, the ratio L/W must be greater than 4.

In cases where MMIC 700 is required to have improved performance, such as reduced optical loss, optical cavity 730 must be capable of supporting at least three traveling guided modes ($m \geq 3$), such as guided modes 810, 820, and 830. In such cases, for a 50:50 coupler, the ratio L/W must be greater than 3 and for a 0:100, the ratio L/W must be greater than 6.

Referring back to FIG. 6, optical microcavity 640 is capable of primarily supporting one or more resonant, such as resonant standing-wave, modes. In some cases, the ratio $L_3/W_3$ is not greater than about 10, or not greater than about 6, or not greater than about 5, or not greater than about 4, or not greater than about 3, or not greater than about 2. In some other cases, the ratio $L_3/W_3$ is not greater than about 1, or not greater than about 0.8, or not greater than about 0.5, or not greater than about 0.3, or not greater than about 0.1. In some cases, optical microcavity 640 is a rectangular cavity similar to optical microcavity 140.

In some cases, $L_3$ is not greater than about 50 microns, or not greater than about 30 microns, or not greater than about 20 microns, or not greater than about 10 microns. In some other cases, $L_3$ is not greater than about 5 microns, or not greater than about 3 microns, or not greater than about 2 microns, or not greater than about 1 micron. In some other cases, $L_3$ is not greater than about 0.8 microns, or not greater than about 0.6 microns, or not greater than about 0.5 microns.

In some cases, optical microcavity 640 is capable of primarily supporting no more than 100 resonant modes, or no more than 50 resonant modes, or no more than 20 resonant modes, or no more than 15 resonant modes, or no more than 10 resonant modes, or no more than 8 resonant modes, or no more than 5 resonant modes.

In some cases, optical microcavity 640 is capable of primarily supporting at least one resonant mode, or at least 2 resonant modes, or at least 5 resonant modes, or at least 10 resonant modes. In some cases, optical microcavity 640 is capable of primarily supporting a single resonant mode, or two resonant modes.

In some cases, microresonator system 600 is designed to operate primarily in a wavelength range from about 0.3 microns to about 15 microns, or from 0.3 microns to about 5 microns, or from about 0.3 microns to about 2 microns, or from about 0.4 microns to about 1.6 microns, or from about 0.6 microns to about 1.6 microns. In some cases, microresonator system 600 is designed to operate primarily at about 633 nm, or at about 850 nm, or at about 980 nm, or at about 1310 nm, or at about 1550 nm, or at about 10,600 nm.

In the exemplary microresonator system 600, optical waveguide 620 optically couples to optical microcavity 640 by core coupling. In general, optical waveguide 620 can optically couple to optical microcavity 640 using any coupling mechanism that may be suitable in an application. For example, optical waveguide 620 can optically couple to optical microcavity 640 by evanescent coupling.

In the exemplary microresonator system 600, optical microcavity 640 optically couples to optical microresonator 650 by evanescent coupling. In general, optical microcavity 640 can optically couple to optical microresonator 650 using any coupling mechanism that may be suitable in an application. For example, optical microcavity 640 can optically couple to optical microresonator 650 by core coupling as shown schematically in, for example, FIG. 1.

Figure 9:
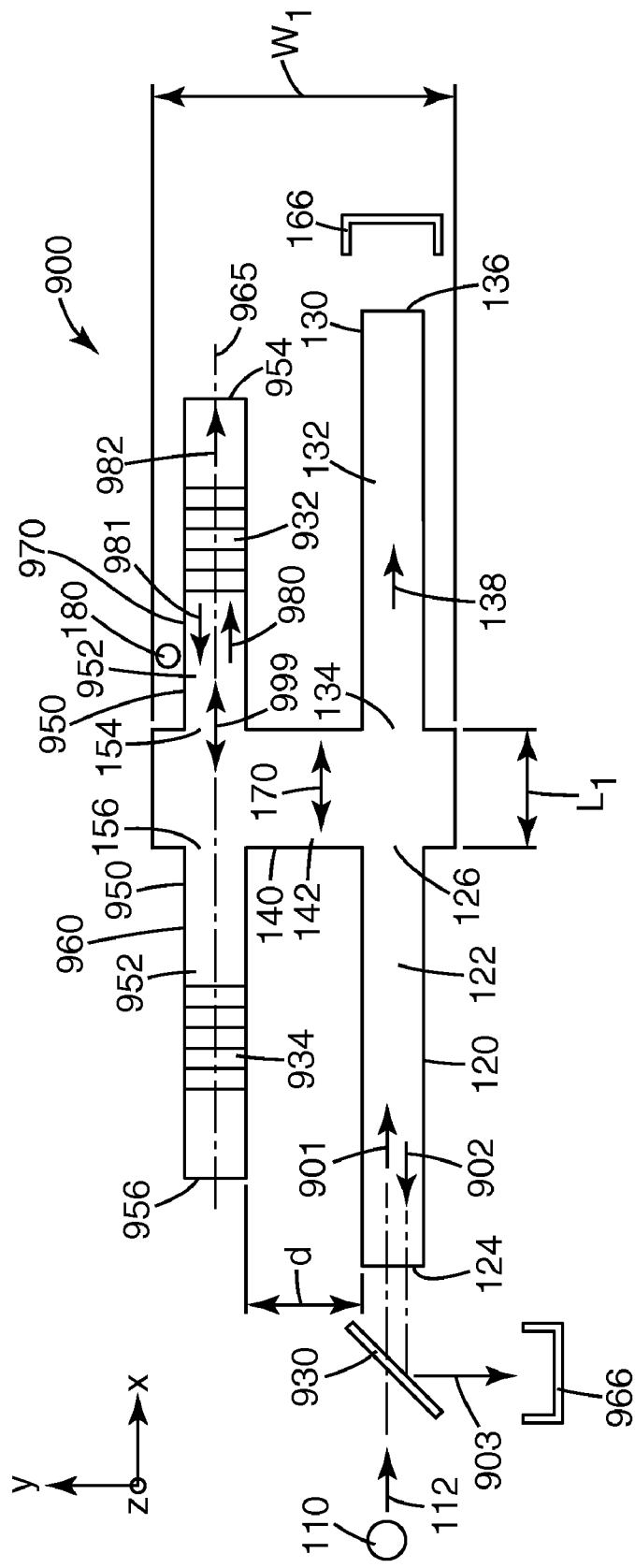
FIG. 9 is a schematic top-view of a microresonator system.

FIG. 9 illustrates a schematic top-view of a microresonator system 900 similar to microresonator system 100 except that optical microresonator 150 is replaced with an optical microresonator 950. Optical microresonator 950 is capable of supporting a resonant mode 999 and includes a core 952, a third optical waveguide 960, and a fourth optical waveguide 970. Third optical waveguide 960 is optically coupled by core coupling to optical microcavity 140 through second face 156 and includes a first grating 934 and a first end face 956. Fourth optical waveguide 970 is optically coupled by core coupling to optical microcavity 140 through first face 154 and includes a second grating 932 and a second end face 954. Third and fourth optical waveguides 960 and 970 are centered on an optical axis 965. Each of first and second gratings 934 and 932 includes a periodic refractive index along optical axis 965. In some cases, the periodicity can be due to a periodic structure, for example, etched into or deposited onto a waveguide. In some other cases, the periodicity can be due to, for example, a periodic variation in the refractive index in a structurally smooth waveguide.

Gratings 932 and 934 are designed to substantially reflect light at one or more or a range of wavelengths. For example, grating 932 can reflect a substantial portion of an incident light 980 as reflected light 981 and transmit the rest as transmitted light 982. In the case of a resonant standing-wave mode 999, the standing-wave may include traveling-wave guided modes 980 and 981 traveling in opposite directions.

In some cases, gratings 932 and 934 are Bragg gratings or distributed Bragg gratings or reflectors (DBR) capable of substantially reflecting light within a narrow wavelength range $\Delta\lambda$ and substantially transmitting light outside $\Delta\lambda$.

In some cases, gratings 932 and 934 are designed to substantially reflect light at an operating wavelength, such as a resonant wavelength, of microresonator system 900. For example, light source 110 emits light at a wavelength $\lambda_a$, such as 850 nm, and gratings 932 and 934 are designed to substantially reflect light at $\lambda_a$, where $\lambda_a$ can correspond to a resonant mode of microresonator system 900.

Gratings or DBRs 932 and 934 define a Fabry Perot cavity between the two gratings, thereby allowing microresonator 950 to be capable of supporting at least one standing-wave guided mode. In some cases, one or both gratings 932 and 934 can be chirped gratings, or blazed gratings, or square gratings, or sinusoidal gratings. In general, gratings 932 and 934 can be any type gratings having a substantial reflectance.

In some cases, the reflectance of gratings 932 and 934 at an operating wavelength of microresonator system 900 is at least 50%, or at least 70%, or at least 80%.

In the exemplary microresonator system 900, optical microresonator 950 includes mechanisms for reflecting light and forming a standing-wave guided mode by including two DBRs. In general, optical microresonator 950 can reflect light by any method that is suitable in an application. For example, in some cases, gratings 932 and 934 can be eliminated and optical microresonator 950 can be capable of forming a standing-wave guided mode by having substantially reflective first and second end facets 956 and 954, respectively. In some cases, either end facet can be flat or curved.

In some cases, end facets 956 and 954 are primarily specularly reflective. In such cases, end facets 956 and 954 can be capable of diffusely reflecting light, but any such diffuse reflectance is secondary to specular reflectance. In some cases, at least one of the end facets of optical microresonator 950 is at least 50% specularly reflective, or at least 60% specularly reflective, or at least 80% specularly reflective.

In some cases, microresonator system 900 can include gratings 932 and 934 and reflective end facets 956 and 954. For example, in some cases light source 110 may be a broadband light source emitting light in a wavelength range. In such cases, gratings 932 and 934 can be chirped gratings to provide high reflectivity across the wavelength range. The reflective end facets can, for example, reflect any light that is not reflected by the corresponding gratings.

The operating wavelength of microresonator system 900 can be tailored or narrowly defined by adjusting gratings 932 and 934. In some cases, the spacing between gratings 932 and 934 can be reduced to increase the free spectral range of microresonator 950. Reducing the spacing can also result in an overall smaller microresonator system 900.

Microresonator system 900 can include a detector 166 at output face 136 and in optical communication with second optical waveguide 130. In some cases, in place of or in addition to detector 166, a detector 966 can be placed in optical communication with first optical waveguide 120 as shown schematically in FIG. 9.

Light source 110 is capable of emitting light 112, at least a portion of which enters optical waveguide 120 through input face 124 of the waveguide and propagates along the positive x-axis as guided mode 901. Guided mode 901 is capable of exciting resonant mode 170 of microcavity 140. Mode 170 is, in turn, capable of exciting guided mode 138 of waveguide 130 propagating along the positive x-axis, guided mode 902 of waveguide 120 propagating along the negative x-axis, and resonant mode 999 of optical microresonator 950.

Optical element 930 redirects at least a portion of light 902 as light 903 towards detector 966. Scattering center 180 is optically coupled to optical microresonator 950 and can induce a change in a characteristic of guided mode 902. Detector 966 can detect the presence of scattering center 180 by detecting the change in the characteristic.

Optical element 930 redirects by, for example, reflecting at least a portion of light 902 along the y-axis while transmitting at least a portion of input light 112. Optical element 930 can be a beam splitter. As another example, optical element 930 can be an optical circulator.

In the exemplary microresonator system 100 shown in FIG. 1, optical waveguides 120 and 130 optically couple to microcavity 140 by core coupling and not evanescent coupling. The optical coupling between microcavity 140 and microresonator 150 is a core coupling. In general, the optical coupling can be a core coupling or an evanescent coupling.

In the exemplary microresonator system 100, the optical coupling between, for example, waveguide 120 and microcavity 140 is a lateral coupling and not a vertical coupling. In general, the optical coupling can be a lateral or vertical coupling as described in, for example, commonly-owned U.S. patent application Ser. No. 11/565,935 which is incorporated herein by reference in its entirety.

In some cases, waveguides 120 and 130, microresonator 150, and microcavity 140 can be integrated onto a common substrate. The integration may be a monolithic integration, in which case the different components are all fabricated onto the common substrate typically using the same material systems. Such an integration can be substrate specific, meaning that the integration may be easier or feasible for some substrates and harder or not possible for some other substrates. For example, it may be possible to fabricate or grow the detector, the microresonator, the microcavity, and the waveguides onto a substrate, such as a Si substrate, but it may be difficult or not possible to grow or fabricate the light source onto the same substrate. As another example, it may be possible to grow or fabricate all the system components on a III-V semiconductor substrate such as an InP or GaAs substrate.

The integration can be a hybrid integration, in which case at least some of the components are first fabricated separately and then assembled onto a common substrate. The assembly can be done by, for example, adhesively bonding the detector and the light source onto the substrate. In such a case, the microresonator, the microcavity, and the waveguides may be monolithically integrated onto the substrate. In some cases, the bonding may require active alignment of the light source and the detector with the waveguide(s).

Figure 10:
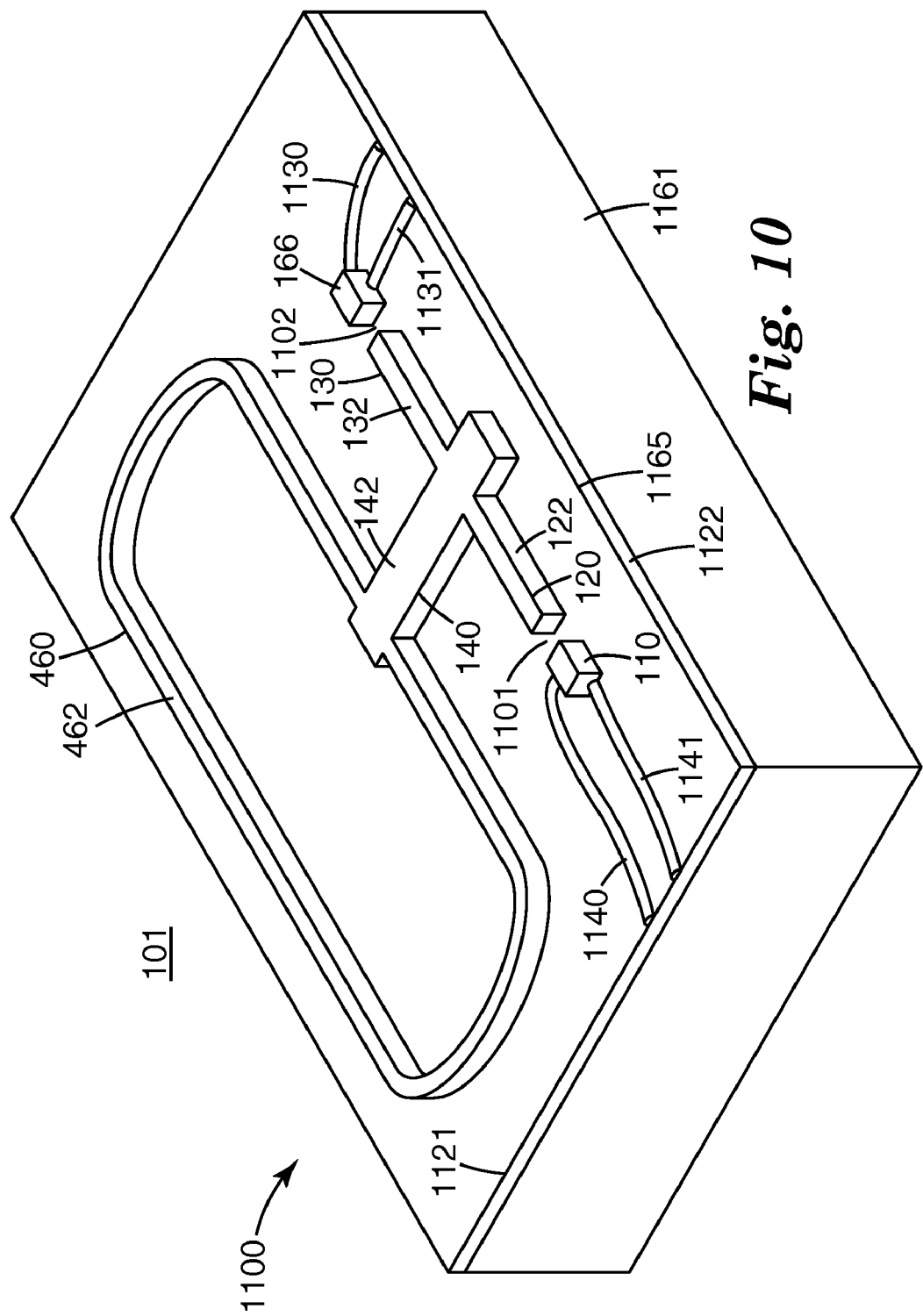
FIG. 10 is a schematic three-dimensional view of an integrated optical device.

FIG. 10 shows a schematic three-dimensional view of an integrated optical device 1100. Light source 110 and detector 166 are integrated onto substrate 1161 of optical device 1100. Waveguides 120 and 130, microcavity 140, and racetrack microresonator 460 have upper cladding 101 and lower cladding layer 1165 and are integrated onto substrate 1161. Light source 110 is separated from waveguide 120 by a gap 1101 and includes electric leads 1140 and 1141 integrated onto substrate 1161. Electric leads 1140 and 1141 extend to an edge 1121 of optical device 1100 for connection to, for example, an external power source and/or a controller not shown in FIG. 10. Detector 166 is separated from waveguide 130 by a gap 1102 and includes electric leads 1130 and 1131 integrated onto substrate 1161. Electric leads 1130 and 1131 extend to an edge 1122 of optical device 1100 for connection to, for example, an external power source and/or other electronics not shown in FIG. 10.

Substrate 1161 can be rigid or flexible. Substrate 1161 may be optically opaque or transmissive. The substrate may be polymeric, a metal, a semiconductor, or any type of glass. For example, substrate 1161 can be silicon. As another example, substrate 1161 may be float glass or it may be made of organic materials such as polycarbonate, acrylic, polyethylene terephthalate (PET), polyvinyl chloride (PVC), polysulfone, and the like.

Microresonator 150, microcavity 140, and optical waveguides 120 and 130 can be made using known fabrication techniques. Exemplary fabrication techniques include photolithography, printing, casting, extrusion, embossing, and etching, such as reactive ion etching or wet chemical etching. Different layers in microresonator system 100 can be formed using known methods such as sputtering, vapor deposition, flame hydrolysis, casting, or any other deposition method that may be suitable in an application.

In some cases, light source 110 can be a broadband light source emitting, for example, white light. In some cases, light source 110 can be a narrow-band light source such as a tunable narrow-linewidth laser source. In some cases, detector 166 can be a narrow-band detector or the detector can be a spectrally sensitive detector. For example, detector 166 can be a spectrum analyzer. In some cases, detector 166 can be a broadband detector.

Some of the advantages of the disclosed embodiments are further illustrated by the following examples. The particular materials, amounts and dimensions recited in this example, as well as other conditions and details, should not be construed to unduly limit the present invention.

EXAMPLE 1

Figure 5B:
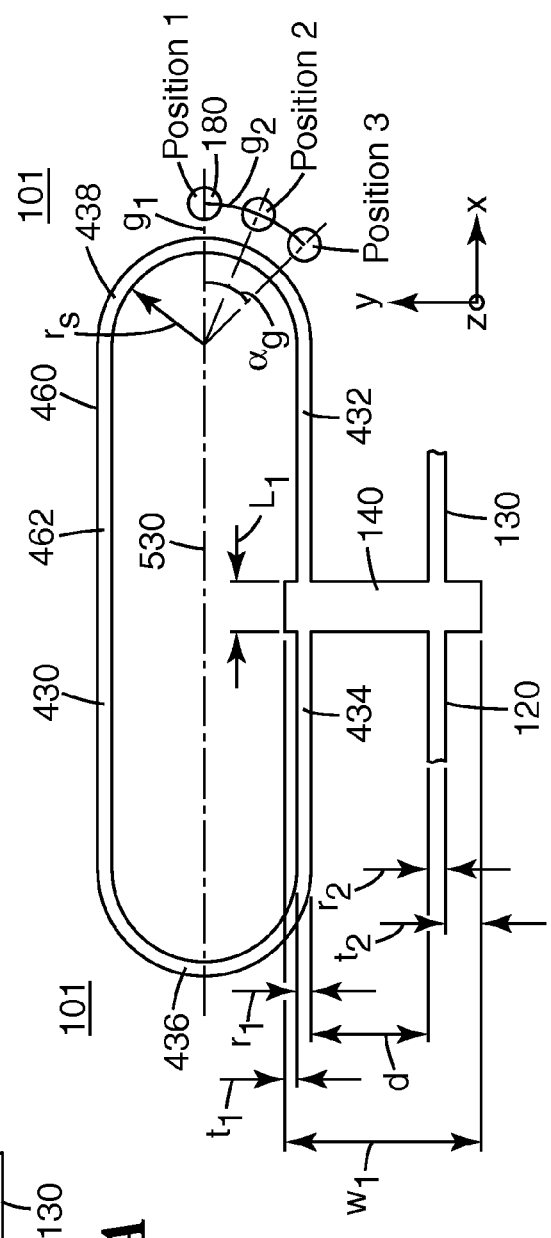

An optical device similar to microresonator system 100 of FIG. 1 and the optical devise shown in FIG. 5B was numerically analyzed using an effective two dimensional Finite Difference Time Domain (FDTD) approach. For the simulation, all the cores were silicon having a refractive index of 3.5 and an effective thickness of 0.4 microns. The optical microresonator was a racetrack having a 4 micron long linear portion 430. The curved portions 436 and 438 were each a semicircle with a 1.6 micron inside radius $r_s$ and a 0.2 micron width resulting in the microresonator having a length $L_2$ of 7.6 microns and a width $W_2$ of 3.6 microns. Each of dimensions $t_1$, $t_2$, $r_1$, and $r_2$ was 0.2 microns. Distance d was 1 micron resulting in a width $W_1$ equal to 1.8 microns. $L_1$ was 0.6 microns resulting in a ratio $L_1/W_1$ of about 0.33. The upper cladding 101 was air having a refractive index of 1. The lower cladding 1165 was silicon dioxide having a refractive index of 1.46.

In the simulation, light source 110 was a pulsed light source emitting light 112 in the form of discrete 1 femtosecond long Gaussian pulses centered at 2 microns with a full width at half maximum (FWHM) of 1 micron. The broadband input pulses resulted in a wide spectrum response in the range from about 1 micron to about 3 microns detected by detector 166.

Figure 11:
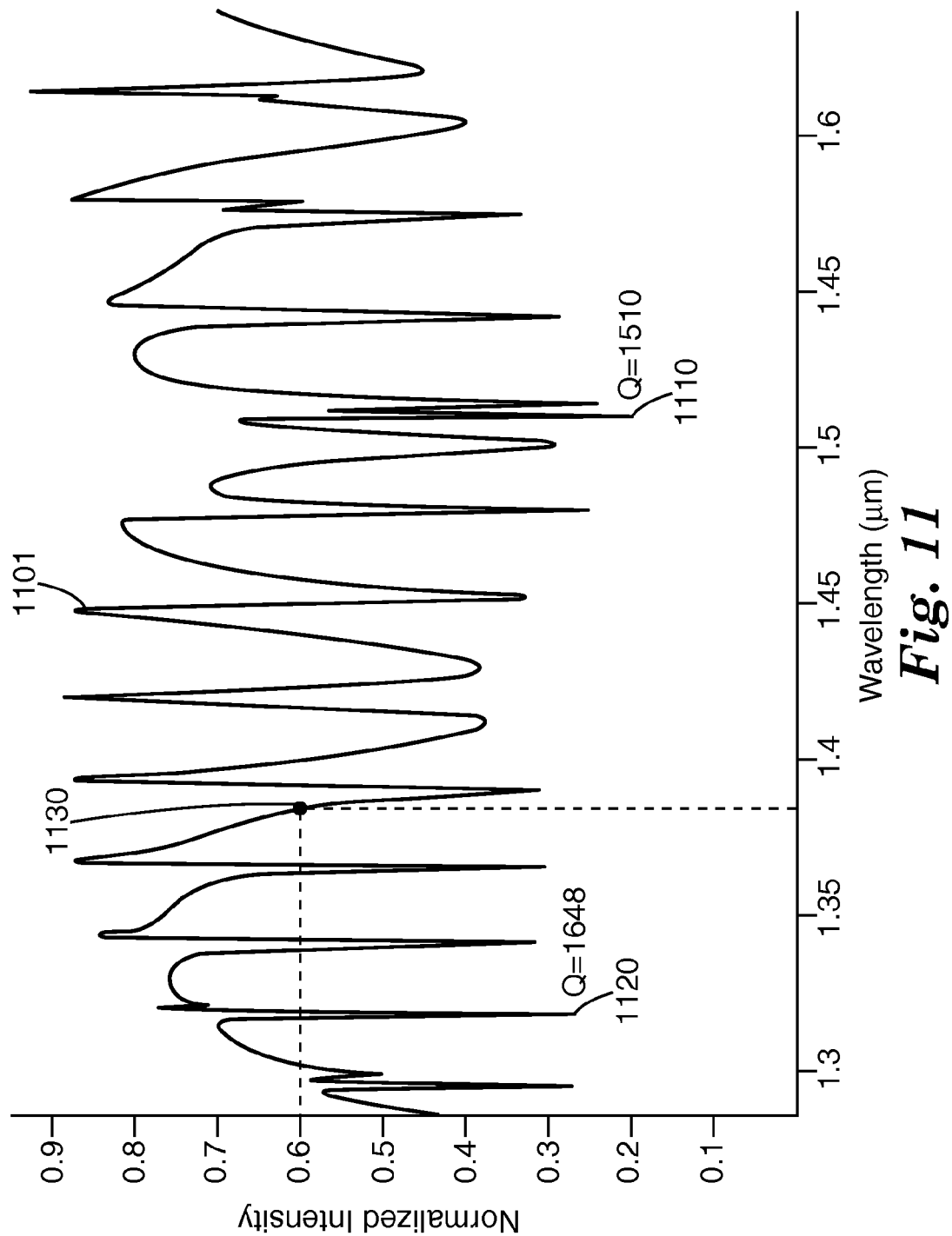
FIGS. 11-14 are plots of calculated signal strength versus wavelength for different microresonator systems without a scattering center.

FIG. 11 shows the calculated signal strength (curve 1101, in arbitrary units relative to the intensity of input light) at detector 166 as a function of wavelength (in microns) in the absence of scattering center 180. As an example, point 1130 on the output plot corresponds to about 60% transmission at about 1.385 microns. Accordingly, at this wavelength about 40% of the input light is lost due to, for example, optical reflection and/or scattering.

FIG. 11 shows that the microresonator system had high Q-factors at several wavelengths. For example, the numerical analysis showed that the Q-factor of the microresonator was 1648 at about 1.32 microns (location 1120) and 1510 at about 1.52 microns (location 1110). Q-factor can be defined as $\lambda_{o1}/\Delta\lambda_{o1}$ where $\lambda_{o1}$ is the center (resonant) wavelength and $\Delta\lambda_{o1}$ is the full width at half maximum (FWHM).

The two dimensional FDTD approach was used to verify that the microcavity supported primarily resonant modes. Light was launched in waveguide 120 at a resonant frequency of the microresonator system and the locations of electric field maxima within the microcavity were monitored as a function of time. The results showed that such locations were essentially stationary, thereby indicating that the microcavity supported primarily resonant standing-wave modes.

EXAMPLE 2

An optical device similar to the device of Example 1 was numerically analyzed using an effective two dimensional FDTD approach except that $L_1$ was 1.2 microns resulting in a ratio $L_1/W_1$ of about 0.67.

Figure 12:
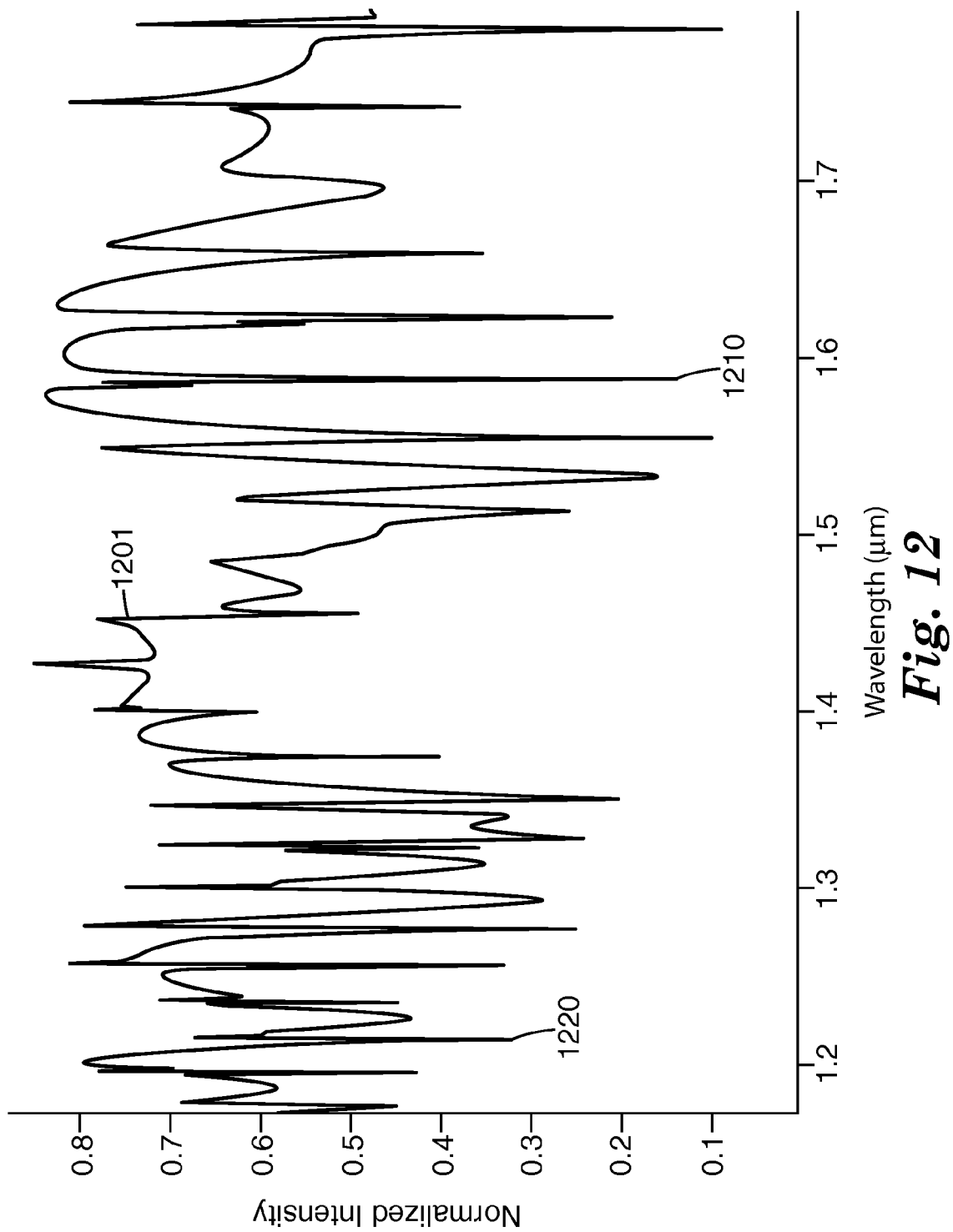

Curve 1201 in FIG. 12 shows the calculated signal strength in arbitrary units relative to the intensity of input light at detector 166 as a function of wavelength in microns in the absence of scattering center 180. FIG. 12 shows that the microresonator system had high Q-factors at several wavelengths. For example, the Q-factor of the microresonator was 2600 at about 1.22 microns (location 1220) and 2263 at about 1.58 microns (location 1210).

A monitoring of the locations of electric field maxima within the microcavity for a resonant mode of the microresonator system as a function of time indicated that the microcavity supported primarily resonant standing-wave modes.

EXAMPLE 3

An optical device similar to the device of Example 1 was numerically analyzed using an effective two dimensional FDTD approach except that d was 1.6 microns resulting in a width $W_1$ of 2.4 microns and a ratio $L_1/W_1$ of 0.25.

Figure 13:
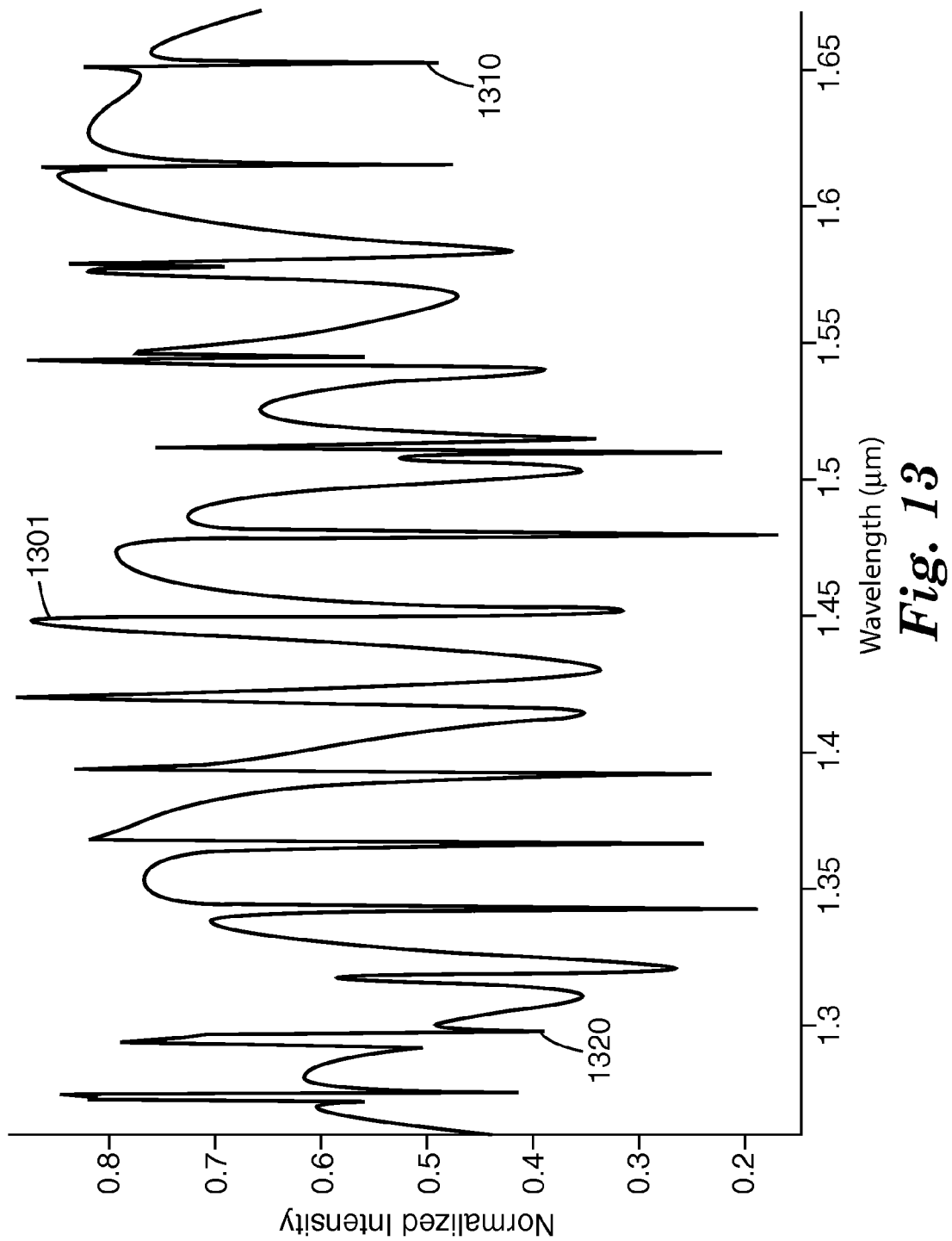

Curve 1301 in FIG. 13 shows the calculated signal strength in arbitrary units relative to the intensity of input light at detector 166 as a function of wavelength in microns in the absence of scattering center 180. FIG. 13 shows that the microresonator system had high Q-factors at several wavelengths. For example, the Q-factor of the microresonator was 1854 at about 1.30 microns (location 1320) and 2203 at about 1.65 microns (location 1310).

A monitoring of the locations of electric field maxima within the microcavity for a resonant mode of the microresonator system as a function of time indicated that the microcavity supported primarily resonant standing-wave modes.

EXAMPLE 4

An optical device similar to the device of Example 1 was numerically analyzed using an effective two dimensional FDTD approach except that d was 2.2 microns resulting in a width $W_1$ of 3.0 microns and a ratio $L_1/W_1$ of 0.2.

Figure 14:
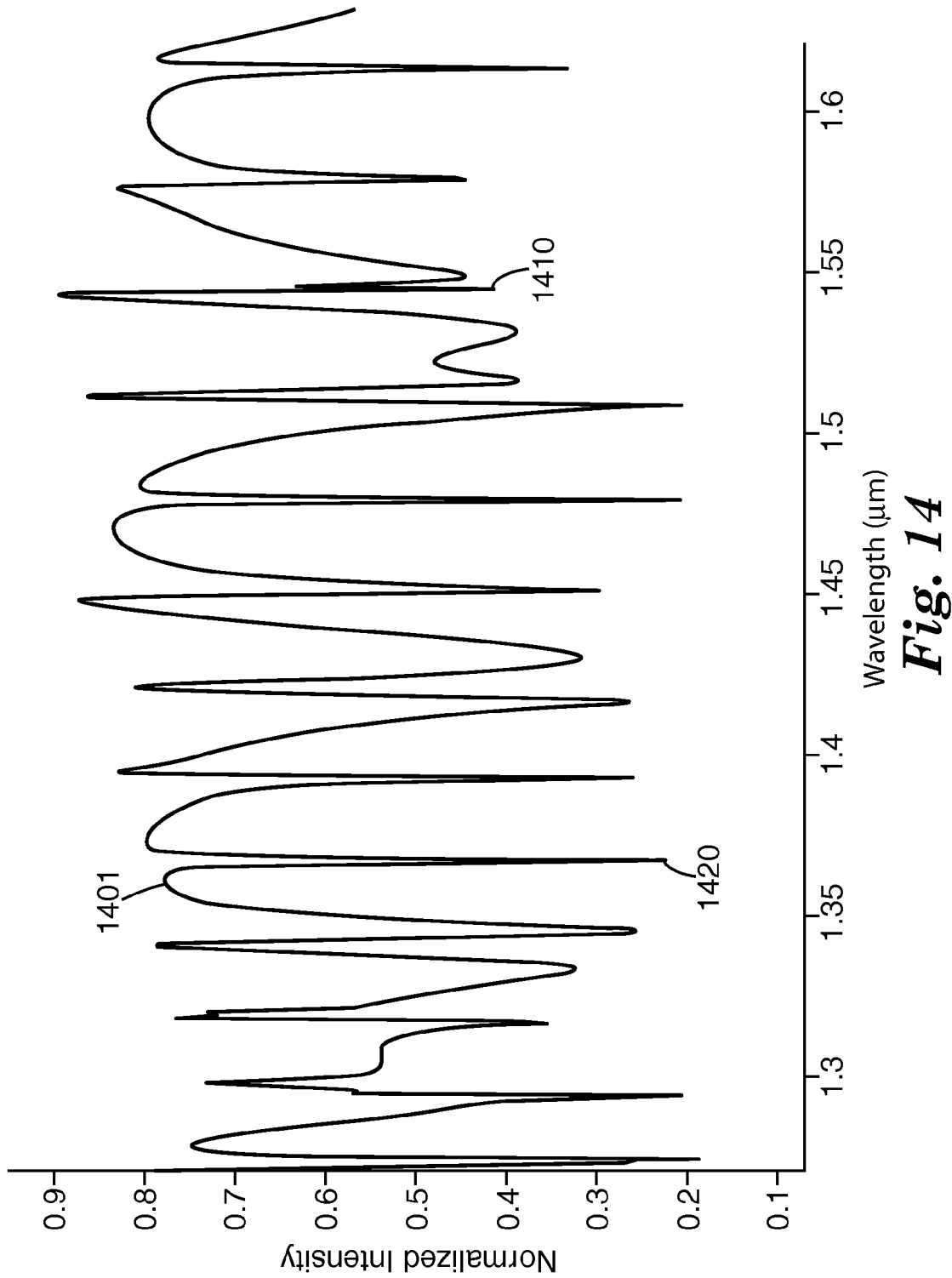

Curve 1401 in FIG. 14 shows the calculated signal strength in arbitrary units relative to the intensity of input light at detector 166 as a function of wavelength in microns in the absence of scattering center 180. FIG. 14 shows that the microresonator system had high Q-factors at several wavelengths. For example, the Q-factor of the microresonator was 1094 at about 1.37 microns (location 1420) and 3090 at about 1.54 microns (location 1410).

A monitoring of the locations of electric field maxima within the microcavity for a resonant mode of the microresonator system as a function of time indicated that the microcavity supported primarily resonant standing-wave modes.

EXAMPLE 5

An optical device similar to the device of Example 1 was numerically analyzed using an effective two dimensional FDTD approach except that d was 2.8 microns resulting in a width $W_1$ of 3.6 microns and a ratio $L_1/W_1$ of about 0.17.

Figure 15:
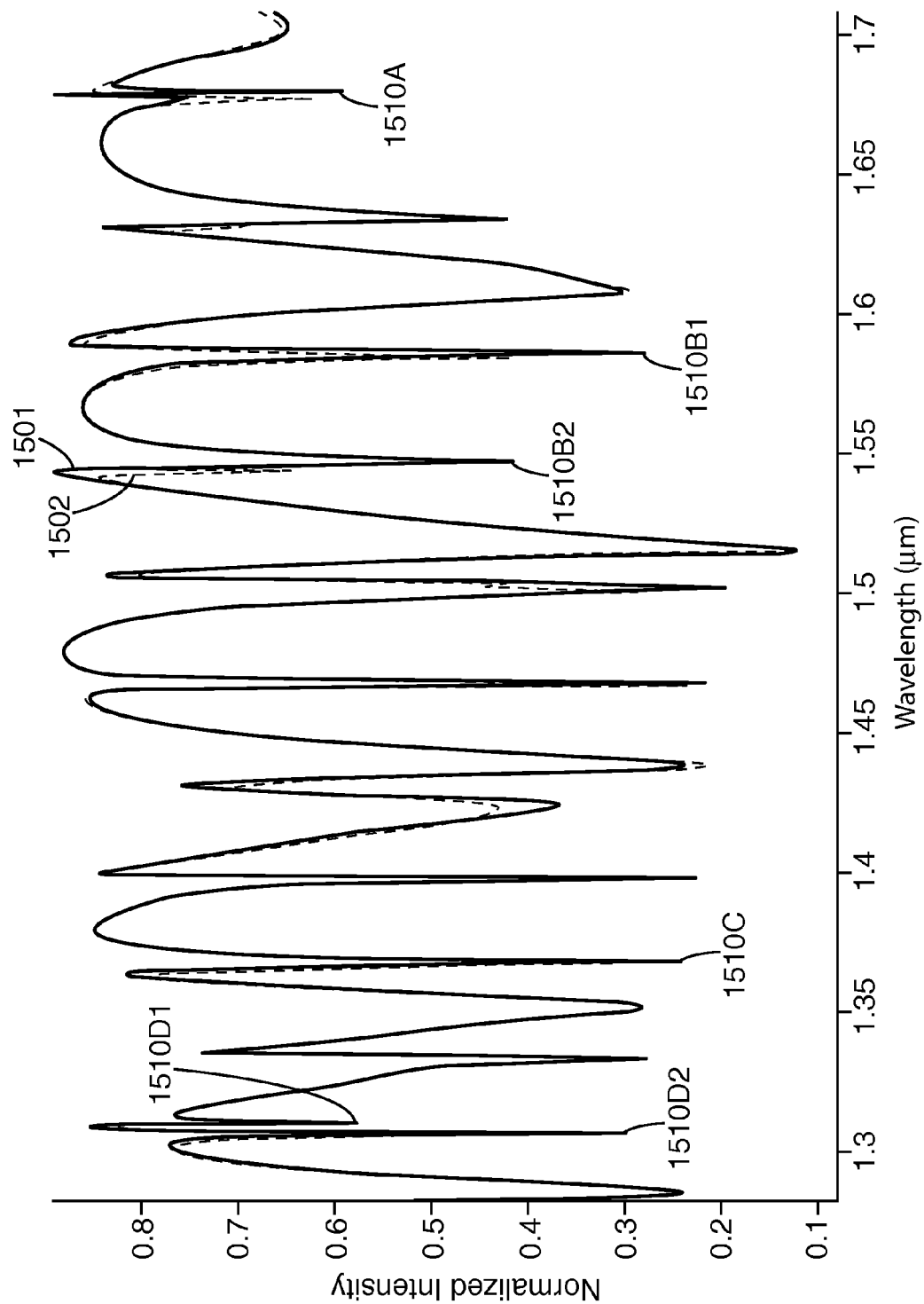
FIG. 15 is a plot of calculated signal strength versus wavelength for a microresonator system with and without a gold scattering center.

Curve 1501 in FIG. 15 shows the calculated signal strength in arbitrary units relative to the intensity of input light at detector 166 as a function of wavelength in microns in the absence of scattering center 180. Curve 1502 shows the calculated output signal strength in the presence of scattering center 180. The scattering center was a spherical gold particle having a diameter equal to 80 nanometers and a complex refractive index equal to 0.54+9.58i at about 1550 nm. The scattering center was placed along a horizontal axis of symmetry 530 of the microresonator (Position 1) as shown schematically in FIG. 5B. There was a gap $g_1$ of 50 nanometers between the particle and the microresonator. FIG. 15 shows that the scattering center induced a shift in at least a number of resonant frequencies of the microresonator system.

Figure 16A:
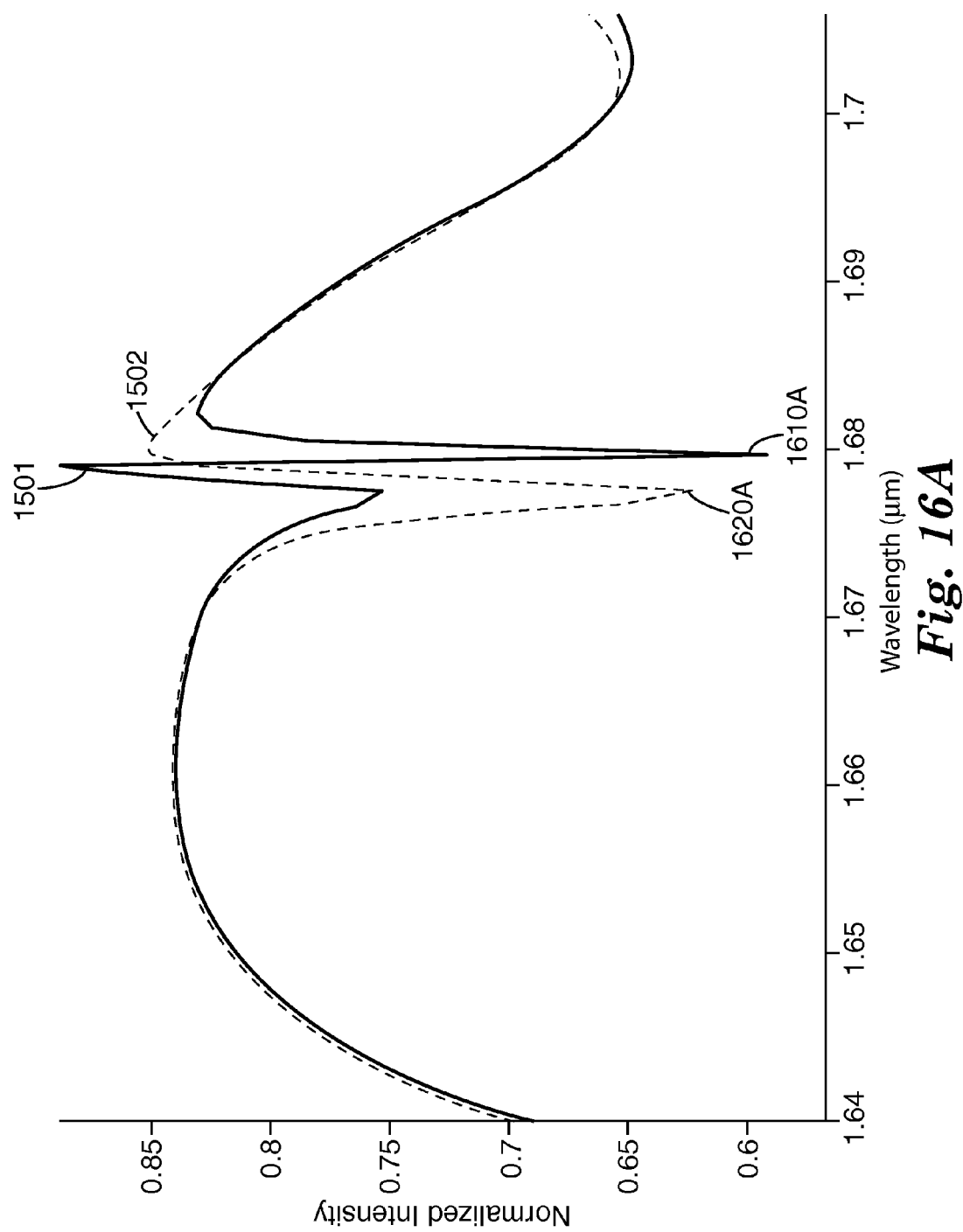
Figure 16B:
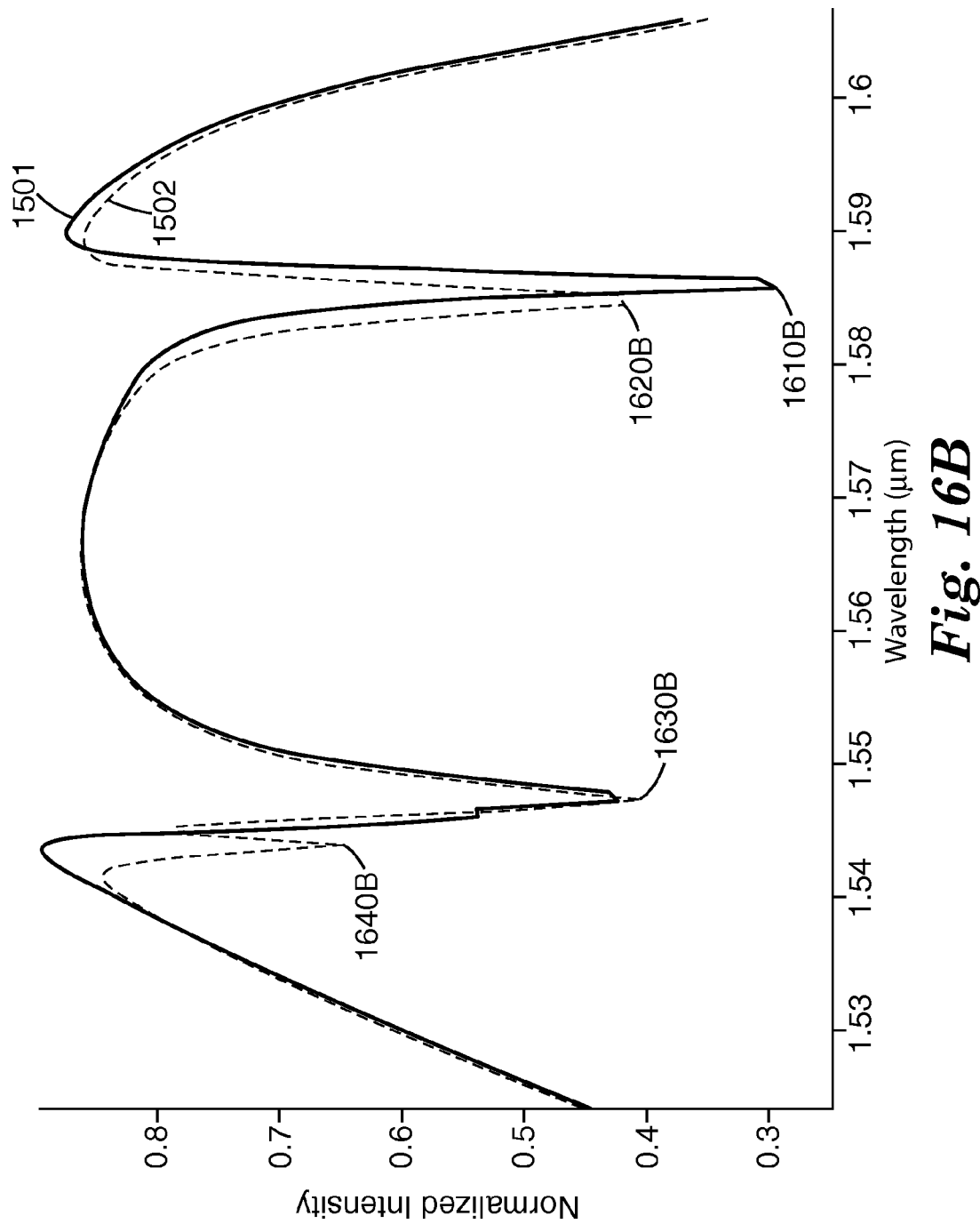

FIG. 16A is an expanded view of curves 1501 and 1502 near 1.68 microns (location 1510A in FIG. 15) showing that scattering center 180 resulted in a relatively large shift of about 2.3 nanometers from peak 1610A with a Q-factor of about 2100 to peak 1620A with a Q-factor of about 840. FIG. 16B is an expanded view of curves 1501 and 1502 near 1.57 microns (locations 1510B1 and 1510B2 in FIG. 15) showing that scattering center 180 resulted in a relatively large shift of about 1.1 nanometers from peak 1610B to peak 1620B and a large shift of about 3 nanometers from peak 1630B to peak 1640B.

Figure 16C:
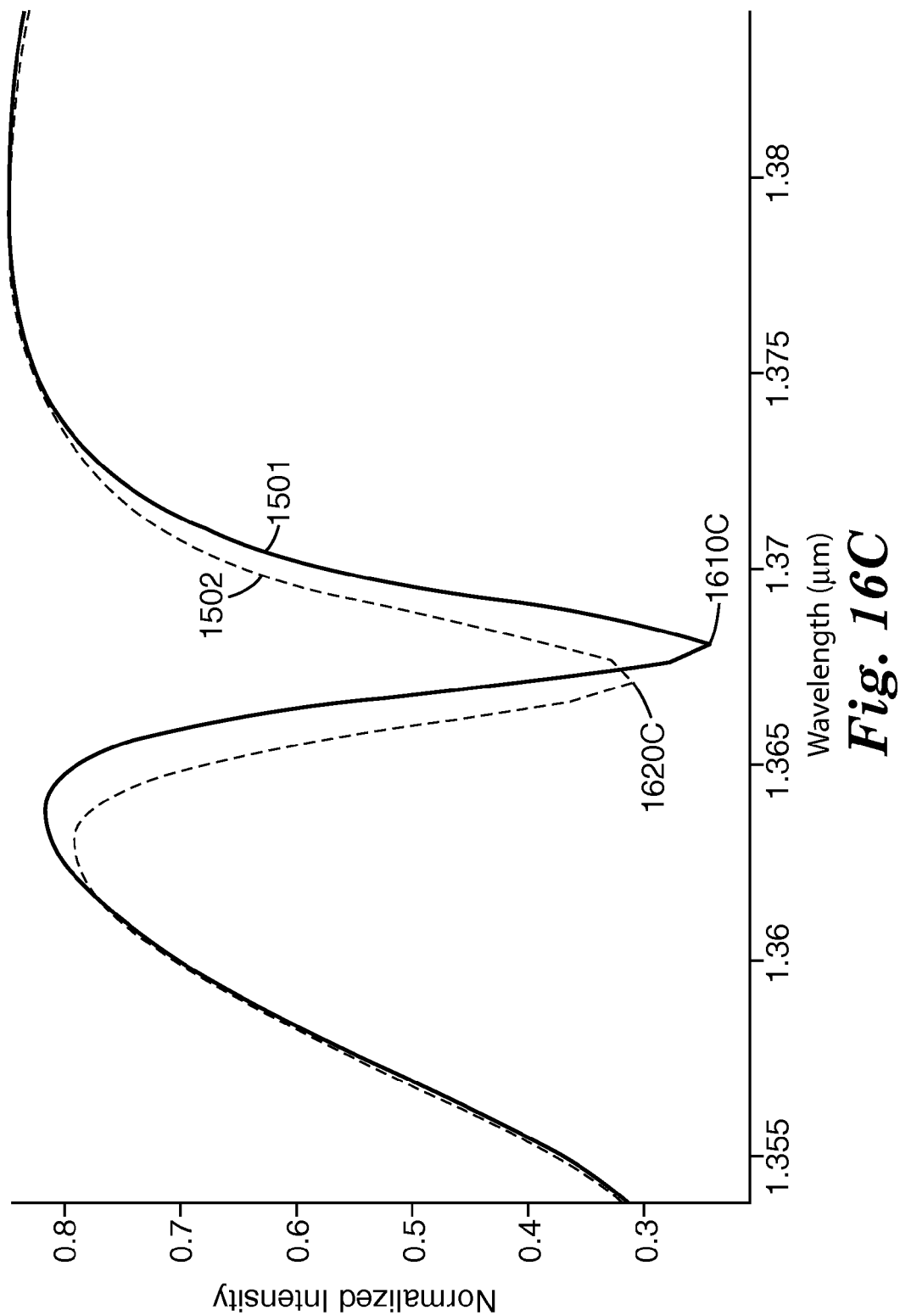

FIG. 16C is an expanded view of curves 1501 and 1502 near 1.37 microns (location 1510C in FIG. 15) showing that scattering center 180 resulted in a relatively large shift of about 1.2 nanometers from peak 1610C to peak 1620C. FIG. 16D is an expanded view of curves 1501 and 1502 near 1.31 microns (locations 1510D1 and 1510D2 in FIG. 15) showing that scattering center 180 resulted in a relatively large shift of about 0.45 nanometers from peak 1610D to peak 1620D and a large shift of about 0.7 nanometers from peak 1630D to peak 1640D.

A monitoring of the locations of electric field maxima within the microcavity for a resonant mode of the microresonator system as a function of time indicated that the microcavity supported primarily resonant standing-wave modes.

EXAMPLE 6

An optical device similar to the device of Example 5 was numerically analyzed using an effective two dimensional FDTD approach except that the gold particle was moved a distance $g_2$=0.42 microns along curved portion 438 to Position 2 in FIG. 5B. Distance $g_2$ was equal to $\lambda/4$ at 1.68 microns, where $\lambda$=1.68 microns corresponded to the resonant frequency of the microresonator system at location 1610A shown in FIG. 16A.

Figure 17:
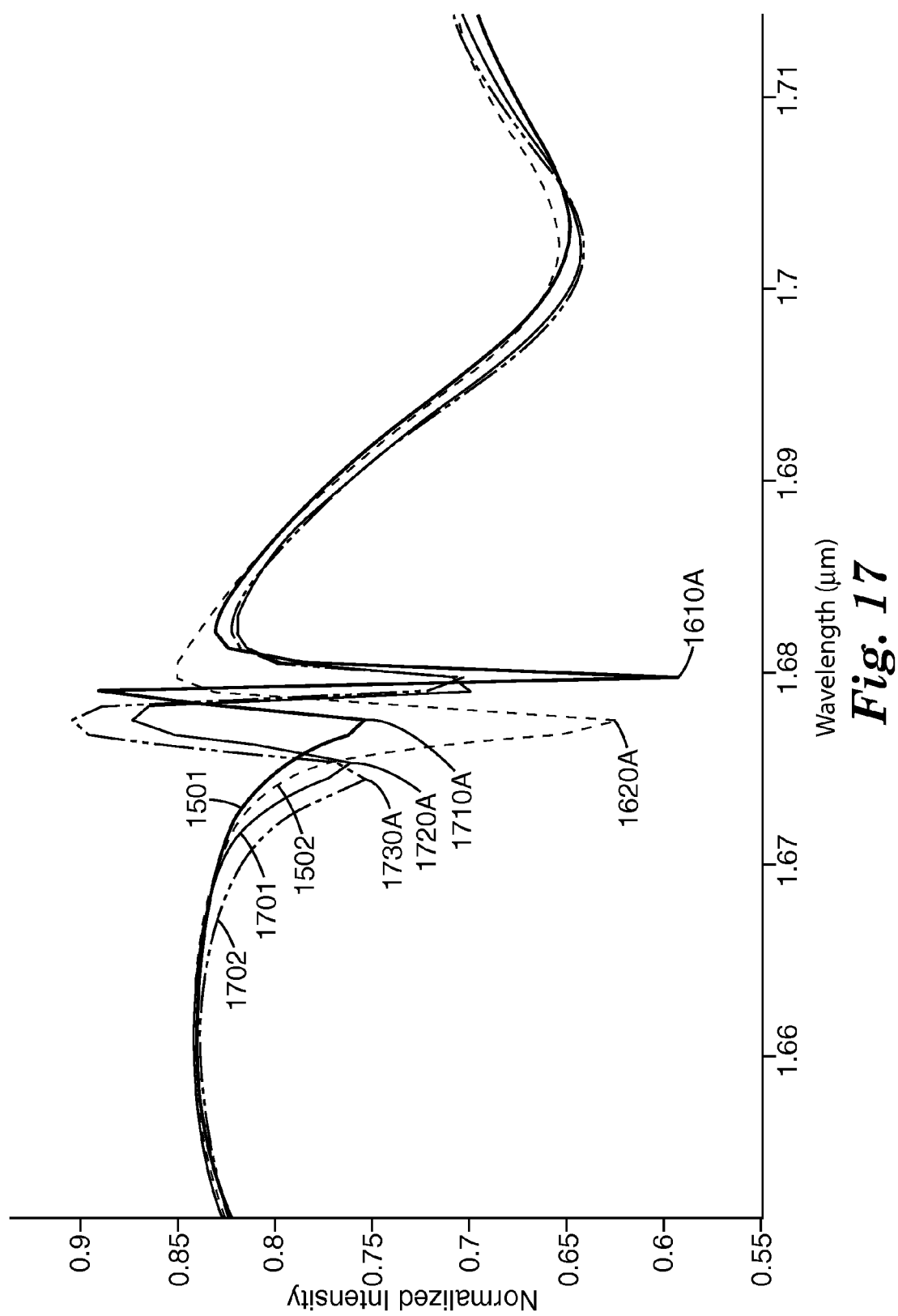
FIG. 17 is a plot of calculated signal strength versus wavelength for a microresonator system without a gold scattering center and with a gold scattering center placed at different locations.

Curve 1702 in FIG. 17 shows the calculated signal strength for the gold particle placed at Position 2. Curve 1702 shows that scattering center 180 resulted in a relatively large shift of about 2.8 nanometers from peak 1710A to peak 1730A.

EXAMPLE 7

An optical device similar to the device of Example 5 was numerically analyzed using an effective two dimensional FDTD approach except that the gold particle was moved along curved portion 438 to Position 3 in FIG. 5B resulting in an angle $\alpha_g$ equal to 45 degrees.

Curve 1701 in FIG. 17 shows the calculated signal strength for the gold particle placed at Position 3. Curve 1701 shows that scattering center 180 resulted in a relatively large shift of about 2.2 nanometers from peak 1710A to peak 1720A.

As used herein, terms such as "vertical", "horizontal", "above", "below", "left" "right", "upper" and "lower", and other similar terms, refer to relative positions as shown in the figures. In general, a physical embodiment can have a different orientation, and in that case, the terms are intended to refer to relative positions modified to the actual orientation of the device. For example, even if the construction in FIG. 10 is inverted as compared to the orientation in the figure, cladding layer 1165 is still considered to be the "lower" cladding layer.

While specific examples of the invention are described in detail above to facilitate explanation of various aspects of the invention, it should be understood that the intention is not to limit the invention to the specifics of the examples. Rather, the intention is to cover all modifications, embodiments, and alternatives falling within the spirit and scope of the invention as defined by the appended claims.

What is claimed is:

1. An optical microresonator system comprising:
   a first optical waveguide capable of supporting a guided mode;
   an optical microcavity optically coupled to the first optical waveguide and capable of supporting primarily one or more resonant modes, the guided mode of the first optical waveguide exciting a first resonant mode of the one or more resonant modes; and
   an optical microresonator optically coupled to the microcavity and capable of supporting a second resonant mode, the first resonant mode exciting the second resonant mode, wherein the first resonant mode comprises a first standing-wave mode and the second resonant mode comprises a second standing-wave mode.

2. The optical microresonator of claim 1, wherein the first standing-wave mode comprises first and second traveling guided modes, wherein the second standing-wave mode comprises first and second traveling guided modes, and wherein:
   the first traveling guided mode of the first standing-wave mode primarily optically couples to the first traveling guided mode of the second standing-wave mode; and
   the second traveling guided mode of the first standing-wave mode primarily optically couples to the second traveling guided mode of the second standing-wave mode.

3. The optical microresonator of claim 1, wherein the microcavity is a rectangular solid.

4. The optical microresonator of claim 1, wherein the microresonator is optically coupled to the microcavity in a first coupling region, the microresonator being a distance d from the waveguide at the first coupling region, the distance defining a first direction, the microcavity having a largest thickness $h_1$ along a second direction orthogonal to the first direction, the microcavity having a largest dimension $W_1$ along the first direction and a largest dimension $L_1$ along a third direction orthogonal to the first and second directions, wherein $L_1/W_1$ is not greater than about 10.

5. The optical microresonator of claim 4, wherein $L_1/W_1$ is not greater than about 5.

6. The optical microresonator of claim 4, wherein $L_1/W_1$ is not greater than about 2.

7. The optical microresonator of claim 4, wherein $L_1/W_1$ is not greater than about 1.

8. The optical microresonator of claim 4, wherein $L_1$ is not greater than about 10 microns.

9. The optical microresonator of claim 4, wherein $L_1$ is not greater than about 5 microns.

10. The optical microresonator of claim 4, wherein the microresonator has a largest dimension $W_2$ along the first direction, a largest thickness $h_2$ along the second direction, and a largest dimension $L_2$ along the third direction, wherein $W_2$ and $L_2$ are substantially equal.

11. The optical microresonator of claim 1, wherein the optical microresonator is one of a microring and a racetrack.

12. The optical microresonator of claim 1, wherein the optical microresonator is a single transverse mode microresonator.

13. The optical microresonator of claim 1, wherein the optical microcavity is capable of supporting no more than 100 resonant modes in a wavelength range from about 0.3 microns to about 5 microns.

14. The optical microresonator of claim 1, wherein the optical microcavity is capable of supporting no more than 20 resonant modes in a wavelength range from about 0.3 microns to about 5 microns.

15. The optical microresonator of claim 1, wherein the optical microcavity is capable of supporting at least two resonant modes in a wavelength range from about 0.3 micron to about 5 microns.

16. The optical microresonator of claim 1 further comprising a second optical waveguide capable of supporting a guided mode and being optically coupled to the optical microcavity.

17. The optical microresonator of claim 16, wherein the first and second optical waveguides are collinear.

18. The optical microresonator system of claim 1, wherein the microcavity is optically coupled to the first waveguide by core coupling, and wherein the microresonator is optically coupled to the microcavity by core coupling.

* * * * *

UNITED STATES PATENT AND TRADEMARK OFFICE
CERTIFICATE OF CORRECTION

PATENT NO.        : 7,486,855 B2
APPLICATION NO.   : 11/616338
DATED             : February 3, 2009
INVENTOR(S)       : Terry L. Smith It is certified that error appears in the above-identified patent and that said Letters Patent is hereby corrected as shown below:

<u>Column 8</u>,
Line 48, delete "λ2" and insert --$\lambda_2$--, therefor.
Line 52, delete "3" and insert --$\lambda_3$--, therefor.

<u>Column 21</u>,
Line 48, before ""right"," insert --,--.

Signed and Sealed this

Thirty-first Day of March, 2009

JOHN DOLL
*Acting Director of the United States Patent and Trademark Office*